US011266332B2

(12) United States Patent
Huang et al.

(10) Patent No.: US 11,266,332 B2
(45) Date of Patent: Mar. 8, 2022

(54) MUTING GLUCOSE SENSOR OXYGEN RESPONSE AND REDUCING ELECTRODE EDGE GROWTH WITH PULSED CURRENT PLATING

(71) Applicant: Medtronic MiniMed, Inc., Northridge, CA (US)

(72) Inventors: Ting Huang, Northridge, CA (US); Ashwin K. Rao, West Hills, CA (US); Rajiv Shah, Rancho Palos Verdes, CA (US); Qingling Yang, Northridge, CA (US)

(73) Assignee: Medtronic MiniMed, inc., Northridge, CA (US)

( * ) Notice: Subject to any disclaimer, the term of this patent is extended or adjusted under 35 U.S.C. 154(b) by 153 days.

(21) Appl. No.: 16/552,780

(22) Filed: Aug. 27, 2019

(65) Prior Publication Data
US 2020/0060586 A1  Feb. 27, 2020

Related U.S. Application Data

(62) Division of application No. 13/779,584, filed on Feb. 27, 2013, now Pat. No. 10,426,383.
(Continued)

(51) Int. Cl.
*A61B 5/145* (2006.01)
*A61B 5/1477* (2006.01)
(Continued)

(52) U.S. Cl.
CPC ........ *A61B 5/14532* (2013.01); *A61B 5/1477* (2013.01); *A61B 5/14865* (2013.01);
(Continued)

(58) Field of Classification Search
CPC ............ A61B 5/14532; A61B 5/14865; A61B 5/1477; A61B 2562/125; C25D 5/18; C25D 3/50; C12Q 1/006; G01N 2333/902
See application file for complete search history.

(56) References Cited

U.S. PATENT DOCUMENTS

| 4,431,004 A | 2/1984 | Bessman et al. |
| 4,490,219 A | 12/1984 | Bindra et al. |

(Continued)

FOREIGN PATENT DOCUMENTS

| EP | 1 153 571 | 11/2001 |
| WO | WO 01/058348 | 8/2001 |

(Continued)

OTHER PUBLICATIONS

Khan G.F, Wernet W; Journal of The Electrochemical Society, vol. 143, No. 10, 1996, pp. 3336-3342 (Year: 1996).*
(Continued)

*Primary Examiner* — Peter Dungba Vo
*Assistant Examiner* — Jose K Abraham
(74) *Attorney, Agent, or Firm* — Gates & Cooper LLP

(57) ABSTRACT

The invention disclosed herein includes amperometric glucose sensors having electrodes formed from processes that electrodeposit platinum black in a manner that produces relatively smooth three dimensional metal architectures, ones that contribute to sensor reliability and stability. Embodiments of the invention provide analyte sensors having such uniform electrode architectures as well as methods for making and using these sensor electrodes. A number of working embodiments of the invention are shown to be useful in amperometric glucose sensors worn by diabetic individuals.

20 Claims, 21 Drawing Sheets

Related U.S. Application Data

(60) Provisional application No. 61/755,345, filed on Jan. 22, 2013.

(51) Int. Cl.
  C25D 5/18 (2006.01)
  A61B 5/1486 (2006.01)
  C12Q 1/00 (2006.01)
  C25D 5/00 (2006.01)
  C25D 3/50 (2006.01)

(52) U.S. Cl.
  CPC .............. C12Q 1/006 (2013.01); C25D 5/18 (2013.01); C25D 5/605 (2020.08); C25D 5/611 (2020.08); *A61B 2562/125* (2013.01); *C25D 3/50* (2013.01); *G01N 2333/902* (2013.01)

(56) References Cited

U.S. PATENT DOCUMENTS

| | | |
|---|---|---|
| 4,562,751 A | 1/1986 | Nason et al. |
| 4,573,994 A | 3/1986 | Fischell et al. |
| 4,678,408 A | 7/1987 | Nason et al. |
| 4,685,903 A | 8/1987 | Cable et al. |
| 4,703,756 A | 11/1987 | Gough et al. |
| 4,755,173 A | 7/1988 | Konopka et al. |
| 4,789,437 A * | 12/1988 | Sing .................. C25D 3/50 205/76 |
| 5,299,571 A | 4/1994 | Mastrototaro |
| 5,390,691 A | 2/1995 | Sproule et al. |
| 5,391,250 A | 2/1995 | Cheney, II et al. |
| 5,482,473 A | 1/1996 | Lord et al. |
| 5,485,408 A | 1/1996 | Blomquist |
| 5,494,562 A | 2/1996 | Maley et al. |
| 5,522,803 A | 6/1996 | Teissen-Simony |
| 5,568,806 A | 10/1996 | Chekney, II et al. |
| 5,605,152 A | 2/1997 | Slate et al. |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 5,985,129 A | 11/1999 | Gough et al. |
| 6,001,067 A | 12/1999 | Shults et al. |
| 6,017,328 A | 1/2000 | Fischell et al. |
| 6,119,028 A | 9/2000 | Schulman et al. |
| 6,120,676 A | 9/2000 | Heller et al. |
| 6,122,536 A | 9/2000 | Sun et al. |
| 6,141,573 A | 10/2000 | Kurnik et al. |
| 6,186,982 B1 | 2/2001 | Gross et al. |
| 6,212,416 B1 | 4/2001 | Ward et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,400,974 B1 | 6/2002 | Lesho |
| 6,512,939 B1 | 1/2003 | Colvin et al. |
| 6,514,718 B2 | 2/2003 | Heller et al. |
| 6,542,765 B1 | 4/2003 | Guy et al. |
| 6,544,212 B2 | 4/2003 | Galley et al. |
| 6,558,351 B1 | 5/2003 | Steil et al. |
| 6,591,876 B2 | 7/2003 | Safabash |
| 6,595,919 B2 | 7/2003 | Berner et al. |
| 6,641,533 B2 | 11/2003 | Causey, III et al. |
| 6,702,857 B2 | 3/2004 | Brauker et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 7,003,336 B2 | 2/2006 | Holker et al. |
| 7,029,444 B2 | 4/2006 | Shin et al. |
| 7,033,336 B2 | 4/2006 | Hogendijk et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 2004/0025238 A1 | 2/2004 | Parsons et al. |
| 2005/0008671 A1 | 1/2005 | Van Antwerp et al. |
| 2005/0115832 A1 | 6/2005 | Simpson et al. |
| 2006/0040157 A1* | 2/2006 | Popov .................. H01M 4/8807 429/483 |
| 2006/0076236 A1 | 4/2006 | Shah et al. |
| 2007/0123819 A1 | 5/2007 | Mernoe et al. |
| 2007/0163894 A1 | 7/2007 | Wang et al. |
| 2007/0227907 A1 | 10/2007 | Shah et al. |
| 2008/0026473 A1* | 1/2008 | Wang .................. C12Q 1/006 436/63 |
| 2010/0025238 A1 | 2/2010 | Gottlieb et al. |
| 2010/0096278 A1* | 4/2010 | Shah .................. C25D 5/10 205/777.5 |
| 2010/0160861 A1 | 6/2010 | Causey, III et al. |
| 2010/0213079 A1* | 8/2010 | Willis .................. A61B 5/14865 205/775 |
| 2011/0152654 A1 | 6/2011 | Wang et al. |
| 2011/0288391 A1* | 11/2011 | Rao .................. A61B 5/6877 600/373 |
| 2011/0319734 A1 | 12/2011 | Gottlieb et al. |

FOREIGN PATENT DOCUMENTS

| | | |
|---|---|---|
| WO | WO 03/022128 | 3/2003 |
| WO | WO 03/022352 | 3/2003 |
| WO | WO 03/023388 | 3/2003 |

(56) References Cited

FOREIGN PATENT DOCUMENTS

| WO | WO 03/023708 | 3/2003 |
|---|---|---|
| WO | WO 03/034902 | 5/2003 |
| WO | WO 03/035117 | 5/2003 |
| WO | WO 03/035891 | 5/2003 |
| WO | WO 03/036255 | 5/2003 |
| WO | WO 03/036310 | 5/2003 |
| WO | WO 03/074107 | 9/2003 |
| WO | WO 04/021877 | 3/2004 |
| WO | WO 08/042625 | 4/2008 |

OTHER PUBLICATIONS

Kim, C.S and Oh, S.M.; Electrochimica Acta, vol. 41, Issue 15, 1996, pp. 2433-2439 (Year: 1996).*
Chandrasekar et al., "Pulse and pulse reverse plating—Conceptual, advantages and applications." Electrochimica Acta 53.8 (2008): 3313-3322.
Feltham et al., "Platinized platinum electrodes." Chemical Reviews 71.2 (1971): 177-193.
Wei et al., "Electrodepositing Pt by modulated pulse current on a Nafion-bonded carbon substrate as an electrode for PEMFC." The Journal of Physical Chemistry C 111.42 (2007): 15456-15463.
PCT International Search Report and Written Opinion dated Oct. 21, 2013 for PCT Application No. PCT/US2013/042754.
Kloke, Ame, et al., "Strategies for the Fabrication of Porous Platinum Electrodes", Advanced Materials, 2011, pp. 4976-5008, vol. 23, No. 43. XP055082182.

\* cited by examiner

MUTING GLUCOSE SENSOR OXYGEN RESPONSE AND REDUCING ELECTRODE EDGE GROWTH WITH PULSED CURRENT PLATING

CROSS REFERENCE TO RELATED APPLICATIONS

This application is a divisional application which claims the benefit under 35 U.S.C. § 120 and § 121 of States patent application Ser. No. 13/779,584, filed Feb. 27, 2013, which claims priority under Section 119(e) from U.S. Provisional Application Ser. No. 61/755,345, filed Jan. 22, 2013, the contents of which are incorporated herein by reference.

TECHNICAL FIELD

The invention relates to analyte sensors such as glucose sensors useful in the management of diabetes.

BACKGROUND OF THE INVENTION

Electrochemical sensors are commonly used to detect or measure the concentrations of in vivo analytes, such as glucose. Typically in such analyte sensing systems, an analyte (or a species derived from it) is electro-active and generates a detectable signal at an electrode in the sensor. This signal is then correlated with the presence or concentration of the analyte within a biological sample. In some conventional sensors, an enzyme is provided that reacts with the analyte to be measured, the byproduct of the reaction being qualified or quantified at the electrode. In one conventional glucose sensor, immobilized glucose oxidase catalyzes the oxidation of glucose to form hydrogen peroxide, which is then quantified by amperometric measurements (e.g. change in electrical current) through one or more electrodes.

A variety of electrochemical glucose sensors are multi-layered, comprising electrodes on top of and/or coated by layers of various materials. Multilayered sensors have a number of desirable properties including the fact that the functional properties of such sensors can be tailored by altering certain design parameters (e.g. number of internal layers, layer thickness, electrodes area and architecture etc). The fabrication of such multilayered sensors can require complicated processes steps that, for example, ensure that the various material layers exhibit appropriate functional characteristics, are of a uniform consistency, and are adapted to adhere to the group of materials that make up a stable sensor stack. In this context, certain electroplating processes can result in plated electrodes having a non-uniform surface, for example one that exhibits excessive growth at electrode edges. This edge growth can then cause non-uniformity in the subsequent layers of materials that are coated onto such electrodes, a phenomena which appears to contribute to certain undesirable glucose sensor phenomena, including layer delamination, sensor signal variability and high oxygen responses.

There is a need for methods and materials that can provide multilayered amperometric sensors with a number of desirable characteristics such as stability and optimized oxygen responses as well as improved manufacturing processes for fabricating such sensors.

SUMMARY OF THE INVENTION

The invention disclosed herein includes electrodes formed from pulse plating processes that are selected to produce highly desirable electrode morphologies. Electrodes formed from these processes exhibit high surface area ratios (SAR) while simultaneously avoiding electrode edge growth, a phenomena observed to occur in conventional plating methods that are used to generate high surface area ratios. Consequently, the pulse plating processes disclosed herein can produce electrodes having increasing surface area ratios without concurrently increasing edge growth. Electrodes having the low edge profiles that are produced by these processes can be coated with various compositions to form relatively smooth and uniform multilayered analyte sensor apparatuses.

The pulsed electrodeposition processes disclosed herein can be used to produce electrodes having a number of desirable material properties that make them well suited for use in amperometric glucose sensors that are worn by diabetic individuals. In particular, conventional sensor electrode plating processes produce electrodes having excessive platinum depositions along the outer edges (edge growth), electrode structures that can cause non-uniformity in the layers of materials that are typically coated over such structures multilayered amperometric sensors. Such irregular features can result in sensors having less than ideal characteristics, including for example, sensor signal variability and high oxygen responses. In contrast, electrodes made by the pulsed processes disclosed herein processes are observed to exhibit a more planar morphology, one characterized by relatively small platinum black growth at the electrode edges. As discussed below, when these electrodes are adapted for use in multilayered glucose sensors, the resultant glucose sensors are shown exhibit a decrease in certain phenomena known to confound accurate glucose sensing in sensors having electrodes with highly irregular morphologies, for example, sensor signal variability and sensor oxygen responses.

The invention disclosed herein has a number of embodiments. One illustrative embodiment is a method of forming a platinum black electrode composition using an electrodeposition process that comprises a plurality of electric current pulses. As shown in the Examples below, the pulsed deposition processes disclosed herein can be tailored to form electrodes selected to have selected material properties that make them very useful as electrodes in multilayered amperometric glucose sensors. For example, platinum electrode compositions produced by these pulsed electrodeposition processes are shown to exhibit less edge growth than platinum electrode compositions generated by processes that employ constant current to produce comparable electrode surface area ratios. As shown in FIG. 6, electrodeposition processes can produce platinum compositions in the form of a predominantly planar layer of material that is surrounded by an edge or ridge of this material (e.g. a ridge that abuts the well in which the composition is electrodeposited). In contrast to electrodes formed from conventional electrodeposition processes that use constant current, in the pulse plated electrodes, the height/thickness of the layer in the edge region is relatively small, and for example, is less than 2× the thickness of the layer of platinum composition that does not form the edge. When used in amperometric glucose sensors, the relatively uniform electrode structures that are produced by pulse electrodeposition are observed to exhibit highly desirable oxygen response profiles. For example, glucose sensors made with pulse plated working electrodes exhibit almost no signal fluctuations in response to changing oxygen concentrations, even at extremely low oxygen levels. In contrast, sensors made with electrodes formed using constant current plating with the same SAR showed as much as 40% signal drop when oxygen levels in a 400 mg/dl glucose solution are changed from 5% to 0.1%.

In illustrative embodiments of the invention, the platinum electrode composition is formed from a process comprising depositing platinum black in the well using a plurality of electric current pulses, for example at least 50, 100, 150, 200 or 250 electric current pulses. In some embodiments of the invention, the current is applied in a certain wave form, for example a monophasic wave, a biphasic wave or a polyphasic wave. The current pulses used in embodiments of the invention can be of the same or of different durations. In the working examples disclosed herein, the duration of the pulses is typically between 0.5 to 10 seconds (e.g. 1 to 5 seconds). Embodiments of the invention can also utilize different amounts of current in the pulse methodologies. For example, in some embodiments of the invention, at least one electrical current density of the pulses is from $-191$ A/m$^2$ to $-267$ A/m$^2$ (e.g. an "on time" current as discussed below). In certain embodiments of the invention, at least one electrical current density of the pulses is from 0 to 25 A/m$^2$ (e.g. an "off time" or "rest time" current as discussed below).

Another embodiment of the invention is an analyte sensor apparatus that includes a base substrate comprising a well that holds a pulse plated platinum electrode composition. In these embodiments, the structure of the platinum composition is formed to include a central planar region and an edge or ridge like region that surrounds the central planar region (see, e.g. FIG. 6). In such embodiments, the thickness or height of the platinum black layer at the edge is less than 2× the average thickness of the platinum black layer in the central planar region. In certain embodiments of the invention, the well comprises a lip that surrounds the well; and the edge region of the platinum black composition is below the lip of the well (see, e.g. FIG. 19B). Typically in these embodiments, both the central planar region and the edge region of the electrode comprise platinum dendrites; and this layer of electrodeposited platinum black forms an electroactive surface of a working electrode in the sensor. Sensor embodiments of the invention typically include additional layers of material coated over the working electrode, for example an analyte sensing layer disposed over the working electrode that detectably alters the electrical current at the working electrode in the presence of an analyte, as well as an analyte modulating layer disposed over the analyte sensing layer that modulates the diffusion of analyte therethrough.

Another embodiment of the invention is a method of sensing an analyte within the body of a mammal. Typically this method comprises implanting an analyte sensor having pulse plated electrodes disclosed herein within the mammal (e.g. in the interstitial space of a diabetic individual), sensing an alteration in current at the working electrode in the presence of the analyte; and then correlating the alteration in current with the presence of the analyte, so that the analyte is sensed. While typical embodiments of the invention pertain to glucose sensors, the electrode architectures disclosed herein can be adapted for use with a wide variety of elements/devices known in the art.

Other objects, features and advantages of the present invention will become apparent to those skilled in the art from the following detailed description. It is to be understood, however, that the detailed description and specific examples, while indicating some embodiments of the present invention are given by way of illustration and not limitation. Many changes and modifications within the scope of the present invention may be made without departing from the spirit thereof, and the invention includes all such modifications.

BRIEF DESCRIPTION OF THE DRAWINGS

As shown in FIG. 11, a potentiostat 300 may include an op amp 310 that is connected in an electrical circuit so as to have two inputs: Vset and Vmeasured. As shown, Vmeasured is the measured value of the voltage between a reference electrode and a working electrode. Vset, on the other hand, is the optimally desired voltage across the working and reference electrodes. The current between the counter and reference electrode is measured, creating a current measurement (isig) that is output from the potentiostat.

FIG. 19A shows an electrode formed from conventional processes that do not use a pulsed current (note the dendrite growth at the edges of the well).

DETAILED DESCRIPTION OF THE INVENTION

Figure 1A:
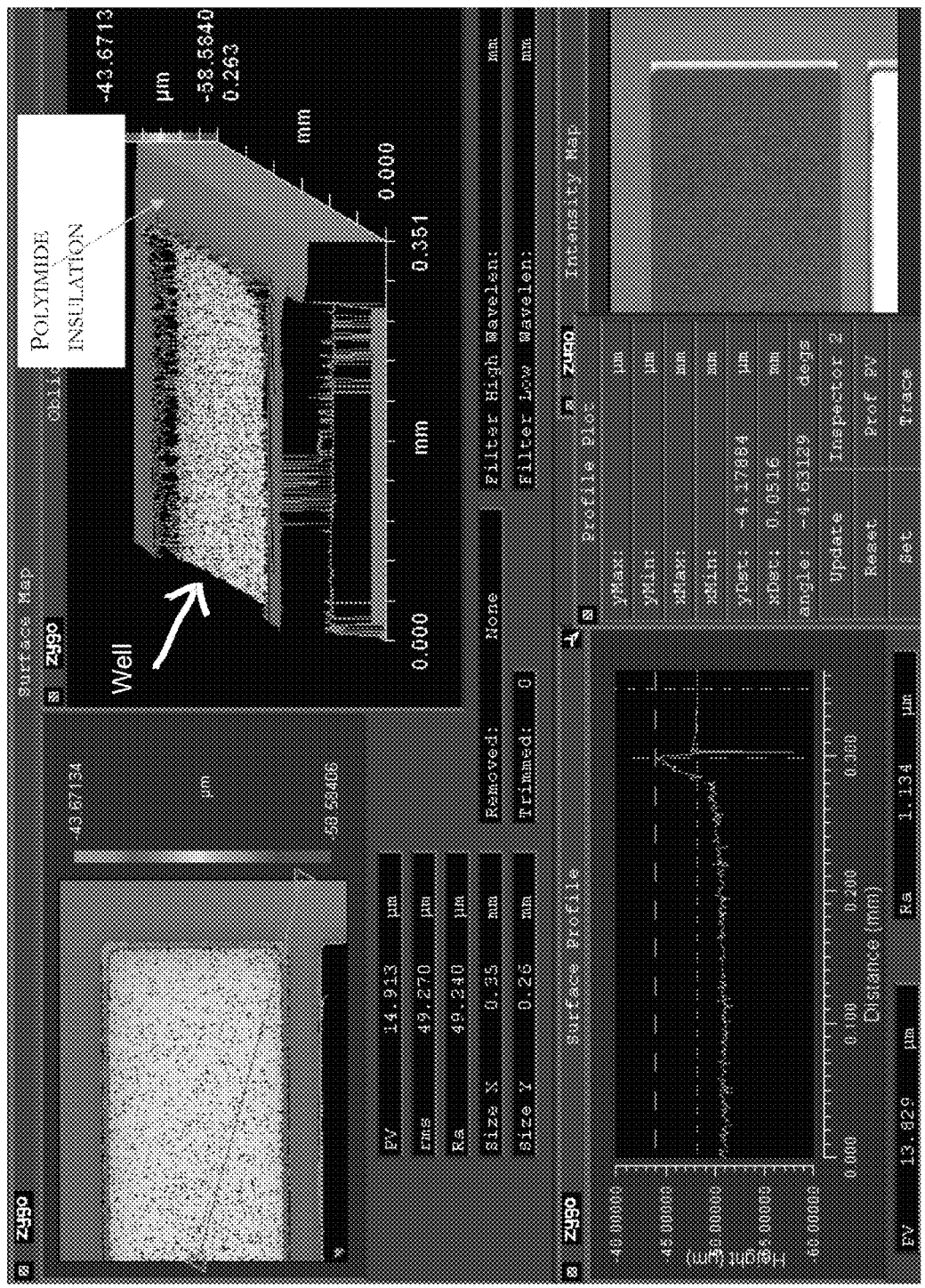
FIG. 1 provides data that characterizes platinum electrode edge growth as measured by a Zygo interferometer. Left, pulse plated working electrode (WE), edge growth (EG)=4 µm; right, Enlite nominal non-pulse plated WE, EG=15 µm. In this description, "Enlite" and "Enlite nominal" and the like refer to electrodes of specific dimension and design made using conventional electrodeposition processes that use constant current (i.e. nonpulsed plating methods). Such comparative disclosures with "Enlite nominal" electrodes made using conventional electrodeposition processes emphasize the desirable features of the pulsed current electrode methods and materials disclosed herein.

Unless otherwise defined, all terms of art, notations, and other scientific terms or terminology used herein are intended to have the meanings commonly understood by those of skill in the art to which this invention pertains. In some cases, terms with commonly understood meanings may be defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

All numbers recited in the specification and associated claims that refer to values that can be numerically characterized with a value other than a whole number (e.g. a thickness) are understood to be modified by the term "about". Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention. Furthermore, all publications mentioned herein are incorporated herein by reference to disclose and describe the methods and/or materials in connection with which the publications are cited. Publications cited herein are cited for their disclosure prior to the filing date of the present application. Nothing here is to be construed as an admission that the inventors are not entitled to antedate the publications by virtue of an earlier priority date or prior date of invention. Further the actual publication dates may be different from those shown and require independent verification.

As discussed in detail below, embodiments of the invention relate to the use of an electrochemical sensor that measures a concentration of an analyte of interest or a substance indicative of the concentration or presence of the analyte in fluid. In some embodiments, the sensor is a continuous device, for example a subcutaneous, transdermal, or intravascular device. In some embodiments, the device can analyze a plurality of intermittent blood samples. The sensor embodiments disclosed herein can use any known method, including invasive, minimally invasive, and non-invasive sensing techniques, to provide an output signal indicative of the concentration of the analyte of interest. Typically, the sensor is of the type that senses a product or reactant of an enzymatic reaction between an analyte and an enzyme in the presence of oxygen as a measure of the analyte in vivo or in vitro. Such sensors typically comprise a membrane surrounding the enzyme through which an analyte migrates. The product is then measured using electrochemical methods and thus the output of an electrode system functions as a measure of the analyte.

Embodiments of the invention disclosed herein provide sensors of the type used, for example, in subcutaneous or transcutaneous monitoring of blood glucose levels in a diabetic patient. A variety of implantable, electrochemical biosensors have been developed for the treatment of diabetes and other life-threatening diseases. Many existing sensor designs use some form of immobilized enzyme to achieve their bio-specificity. Embodiments of the invention described herein can be adapted and implemented with a wide variety of known electrochemical sensors elements, including for example, those disclosed in U.S. Patent Application Nos. 20050115832, 20050008671, 20070227907, 20400025238, 20110319734, 20110152654 and Ser. No. 13/707,400 filed Dec. 6, 2012, U.S. Pat. Nos. 6,001,067, 6,702,857, 6,212,416, 6,119,028, 6,400,974, 6,595,919, 6,141,573, 6,122,536, 6,512,939 5,605,152, 4,431,004, 4,703,756, 6,514,718, 5,985,129, 5,390,691, 5,391, 250, 5,482,473, 5,299,571, 5,568,806, 5,494,562, 6,120,676, 6,542,765, 7,033,336 as well as PCT International Publication Numbers WO 01/58348, WO 04/021877, WO 03/034902, WO 03/035117, WO 03/035891, WO 03/023388, WO 03/022128, WO 03/022352, WO 03/023708, WO 03/036255, WO03/036310 WO 08/042, 625, and WO 03/074107, and European Patent Application EP 1153571, the contents of each of which are incorporated herein by reference.

A. Illustrative Embodiments of the Invention and Associated Characteristics

While conventional electrodeposition processes that use constant current to form platinum black electrodes can produce electrodes having high active surface areas that are useful for electrochemical reactions, these processes also produce electrodes having significant edge growth (see, e.g. FIG. 6B). The dendrite structures that form this edge growth can contribute to non-uniformity in subsequent layers of material that are coated into such electrodes (e.g. layer cracking, layer delamination and the like). Such non-uniformity in a plurality of layered sensor elements can contribute to certain undesirable phenomena such as sensor signal variability and high oxygen response.

As disclosed herein, a new pulsed current plating process for Pt black has been developed, one that produces electrode having the electrochemically robust active surface areas that are similar to those formed in conventional plating processes (i.e. those that utilize constant current) while, at the same time, drastically reduces platinum edge growth. Embodiments of the pulsed current plating processes disclosed herein can be optimized to almost eliminate edge growth while maintaining or even increasing active surface area (even in the absence of a reverse pulse current).

Figure 6:
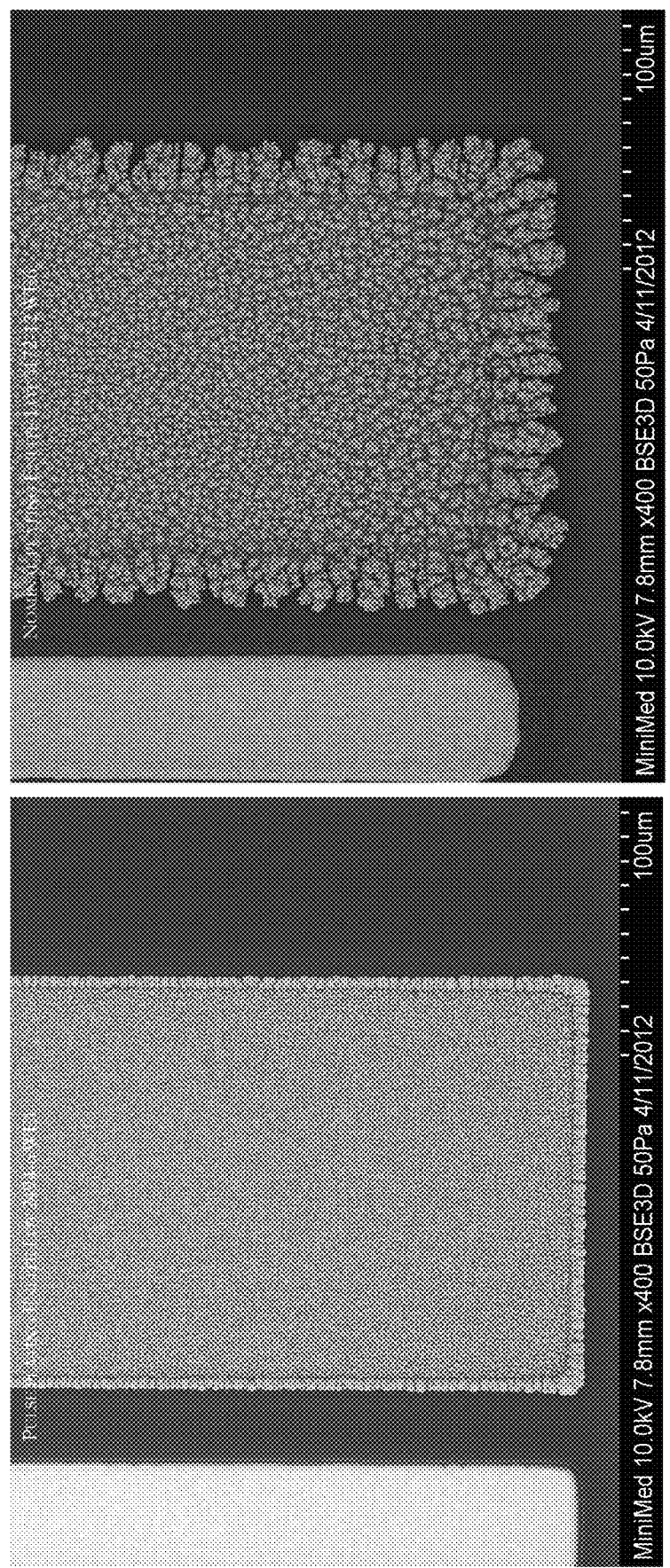
FIG. 6 provides scanning electron microscope (SEM) pictures showing a comparison of WEs at the same magnification: left, pulse plated Enlite electrode ($-75$ µA, 2 sec on, 2 sec off, 150 cycles), right, nominal Enlite non-pulsed plated electrode.
Figure 18:
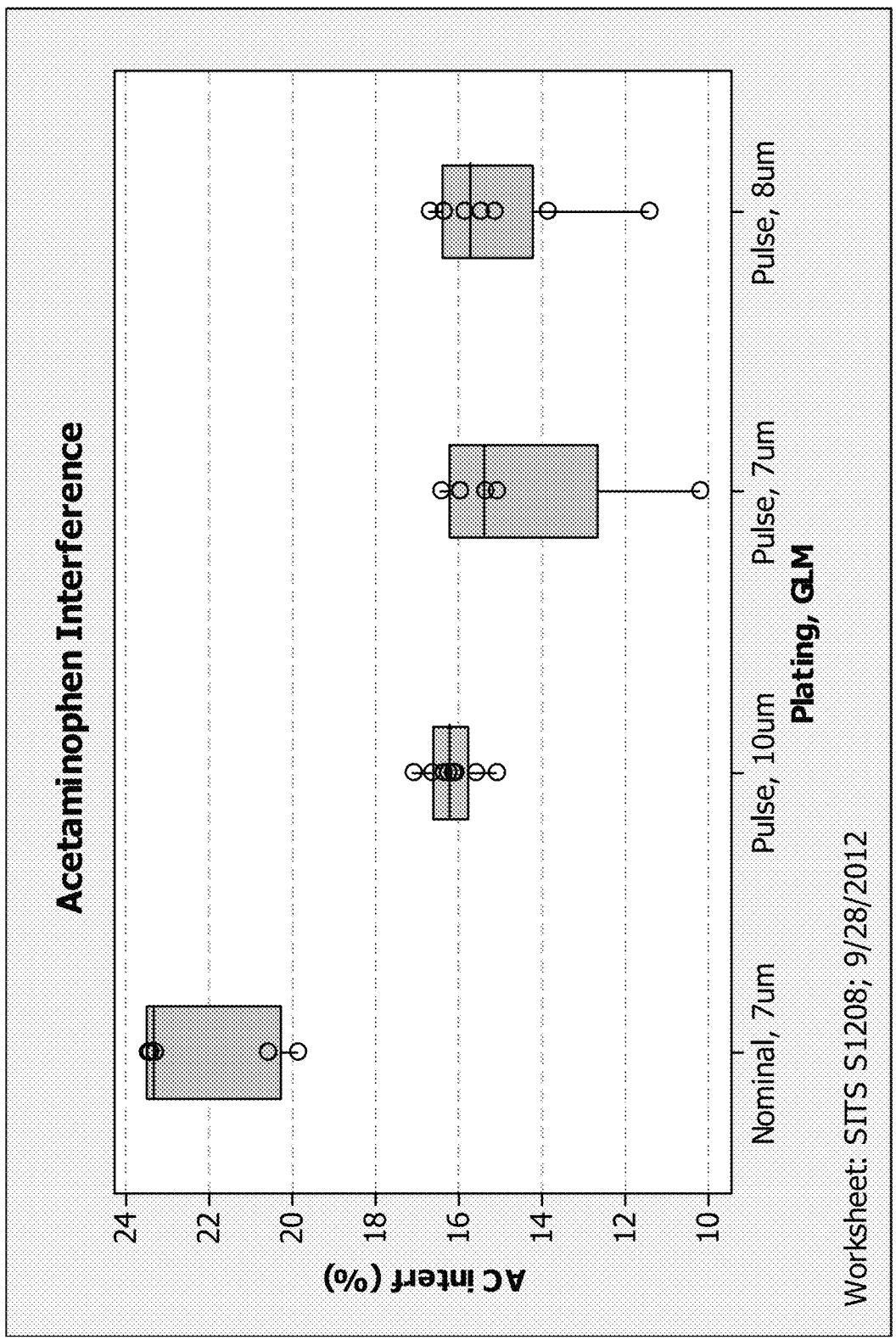
FIG. 18 provides a boxplot of the effect of sensor acetaminophen interference in electrodes made from various pulse plating methods and nonpulsed (nominal) plating methods.

The pulsed electrodeposition processes disclosed herein produce platinum black compositions having material properties that made them very useful as electrodes in multilayered amperometric glucose sensors. For example, platinum electrode compositions produced by these pulsed electrodeposition processes are shown to exhibit surfaces having more uniform morphologies than can be generated by processes that employ constant current. As shown in FIG. 6, embodiments of the invention produce a platinum composition in the form of a planar layer of material that is surrounded by an edge or ridge of platinum (e.g. a ridge that abuts the well in which the composition is electrodeposited). In contrast to electrodes formed from conventional constant current processes, in the pulse plated electrodes, the average thickness of the layer in the edge region is relatively small, and for example, is less than 2× the average thickness of the platinum black layer that is not part of the edge region (the central planar region). In addition, when used in amperometric glucose sensors, these relatively uniform electrode structures are observed to exhibit highly desirable oxygen response profiles. For example, glucose sensors made with pulse plated working electrodes exhibit almost no signal fluctuations in response to changing oxygen concentrations, even at extremely low oxygen levels. In contrast, sensors made with electrodes formed using constant current plating showed as much as 40% signal drop when oxygen levels in a 400 mg/dl glucose solution are changed from 5% to 0.1%. Data illustrating this oxygen responsiveness is presented in FIGS. 15 and 16. Moreover, certain working embodiments of sensors made with electrodes formed using pulse plating processes also show a lower response to interfering species such as acetaminophen. Graphed data which shows the differences in acetaminophen interference in pulse plated and non-pulse plated electrodes is presented in FIG. 18. In addition, in certain embodiments of the invention, electrodes made with pulsed platinum plating techniques have an SAR of at least 250, 275, 300, 325, 350 or 400 (see, e.g. Table 1 below).

An illustrative embodiment of the invention is a method of forming a platinum black electrode composition using an electrodeposition process that comprises a plurality of electric current pulses. As shown in the Examples below, the pulsed deposition processes disclosed herein can be tailored to form electrodes selected to have certain material properties. Optionally, for example, the electrode is made using an electrodeposition process in a well of a base substrate that includes a planar sheet of a conductive material on the bottom of the well (e.g. Au) and a wall of dielectric material (e.g. a polyimide). In illustrative embodiments of the invention, the platinum composition is formed from a process comprising depositing platinum black in the well using a plurality of at least 50, 100, 150, 200 or 250 electric current pulses. In some embodiments of the invention, the current is applied in a certain wave form, for example a monophasic wave, a biphasic wave or a polyphasic wave.

One exemplary pulse plating process uses over 150 pulses (cycles) to generate electrodes with desired surface area ratios and concurrent low edge profiles. In this working embodiment, each of these 150 cycles is identical. Moreover, within each cycle in this embodiment, there's a pulse period and a rest period (see, e.g. FIG. 2). These two periods can have the same or different durations. In this embodiment, the pulse period ("on time") has the higher (negative) current, the rest period ("off time" or "rest time") has zero or very low (positive) current. The time of the current pulses in embodiments of the invention can be of the same duration (e.g. a pulse period lasting one second and a rest period lasting one second) or, alternatively, of different durations (e.g. a pulse lasting one second and a rest period lasting two seconds). In the working examples disclosed herein, the duration of the pulses is typically between 0.5 to 10 seconds (e.g. 1 to 5 seconds). In some embodiments of the invention, electrical current density of the pulses is from $-191$ $A/m^2$ to $-267$ $A/m^2$ during "on time". In this embodiment, electrical current density of the pulses is from 0 to 25 $A/m^2$ during "off time" or "rest time". In some embodiments of the invention, the electrical current of the pulses is from $-60$ µA to $-100$ µA (e.g. $-75$ uA) during on time, from 0 µA to 10 µA during off time. As noted above, the pulse plating processes of the invention typically use at least two currents: one current indicating the height the pulse, and another current at the foot of the pulse. If only one current is specified in a process parameter list, it is implied that, at the foot of the pulse, the current is approximately zero. It does not have to be zero, it can be a small positive number (e.g. 0 µA to 10 µA). Such a small positive current during "rest period" can be used, for example, to dissolve dendrites formed in the plating process and make plating smoother.

Embodiments of the invention include methods for forming analyte sensors that are designed to include the structurally uniform electrodes disclosed herein. One illustrative method comprises providing a base substrate formed from a planar sheet of a dielectric material and having a well disposed therein. This method includes forming a working electrode in the well of the base substrate, wherein the working electrode comprises a platinum composition formed from an electrodeposition process comprising depositing platinum black in the well using a plurality of electric current pulses. In such methods, the platinum composition formed using a plurality of electric current pulses comprises a central planar region having a first thickness and an edge region having a second thickness that surrounds the central planar region. FIG. 6 shows these regions in electrodeposited platinum electrodes. In this context, artisans understand that the edge region in this embodiment is region surrounding the rectangular electrode that comprises more platinum material than the rest of the electrode layer, while the central planar region is the region of the electrode inside of this edge that does not comprise relatively more platinum material. In certain embodiments of the invention, the electrodeposition process is selected to produce a platinum black layer having an average thickness between 1 µm and 20 µm (and typically about 1, 2, 3, 4, 5, 6, 7, 8, 9, or 10 µm) in the central planar region. In certain embodiments of the invention, the electrodeposition process produces a platinum black layer having an edge that is less than 15, 14, 13, 12, 11, 10, 9, 8, 7, 6 or 5 µm in thickness (see, e.g. FIGS. 8 and 9). In some embodiments, the top of the edge region rises less than about 7, 6, 5, 4, 3, 2 or 1 μm above the top of the central planar region. In certain embodiments of the invention, the average thickness of the platinum black layer in the edge region is less than 2×, 1.5× or 1× the average thickness of the platinum black layer not in the edge region (e.g. in the central planar region).

The methods for forming analyte sensors that comprise the electrodes disclosed herein can include a number of other steps. For example, such methods can include forming a working electrode, a counter electrode and a reference electrode on the base substrate and/or forming a plurality of contact pads on the base substrate, and/or forming a plurality of electrical conduits on the base substrate. In certain embodiments of the invention, the methods comprise forming a plurality of working electrodes, counter electrodes and reference electrodes clustered together in units consisting essentially of one working electrode, one counter electrode and one reference electrode are formed on the base substrate and these clustered units are longitudinally distributed on at least one longitudinal arm of the base substrate in a repeating pattern of units. Optionally in such methods, the working electrode is formed as an array of electrically conductive members disposed on the base substrate, the electrically conductive members are circular and have a diameter between 10 μm and 400 μm, and the array comprises at least 10 electrically conductive members. The methods can further comprise forming an analyte sensing layer on the working electrode, wherein the analyte sensing layer detectably alters the electrical current at the working electrode in the presence of an analyte. Typically these methods also include forming an analyte modulating layer on the analyte sensing layer, wherein the analyte modulating layer modulates the diffusion of analyte therethrough.

Another embodiment of the invention comprises a sensor electrode configuration that includes a base substrate comprising a well and a platinum composition disposed in the well. In such embodiments, the platinum composition is disposed in the well as a layer of electrodeposited platinum black that comprise a central planar region having a first thickness and an edge region having a second thickness that surrounds the central planar region. Typically in such electrodes, the average thickness/height of the platinum black layer in the edge region is less than 2×, 1.75×, 1.5×, 1.4×, 1.3×, 1.2× or 1.1× the average thickness/height of the platinum black layer in the central planar region (e.g. for less than 2×, an edge region that is less than about 10 μm thick when a central planar region is about 5 μm thick). In certain embodiments of the invention, the average thickness/height of the platinum black layer in the edge region is less than about 10, 9, 8, 7 or 6 μm. In the working embodiments of the invention that are disclosed herein the central planar region and the edge region comprise platinum dendrites.

Figure 19A:
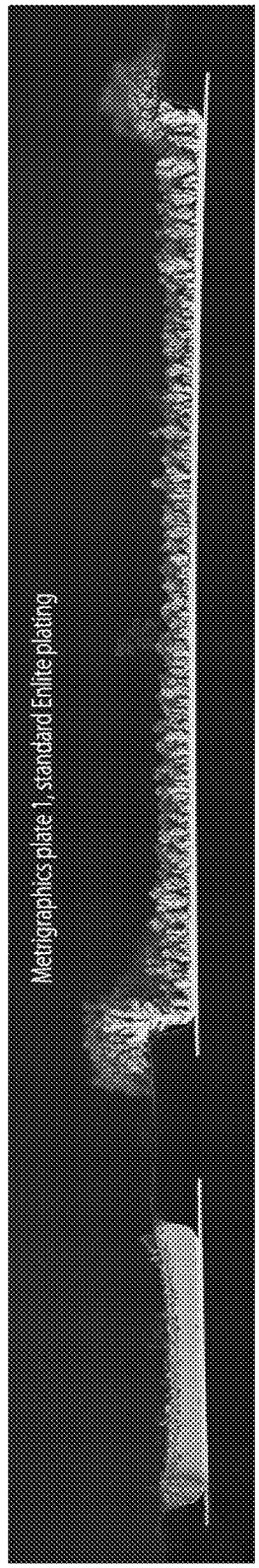
FIGS. 19A and B provide photographs showing a comparison of electrodeposited platinum electrodes formed in a well disposed within a polyimide base substrate.
Figure 19B:
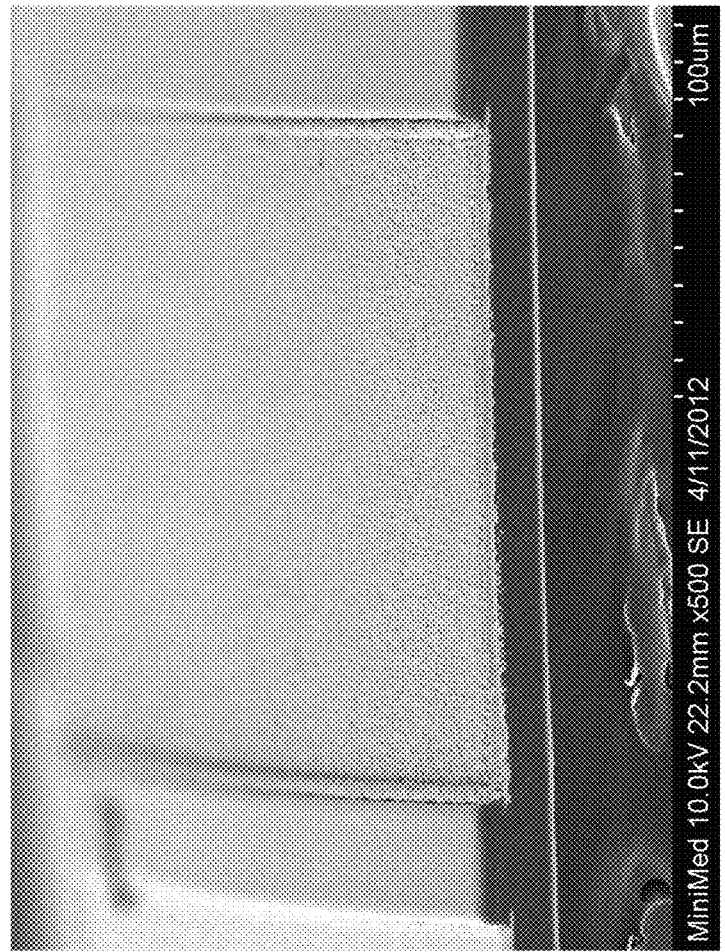
FIG. 19B shows an electrode formed from electrodeposition processes that use a pulsed current (note the edges of the deposited platinum are below the lip of the well).
Figure 20:
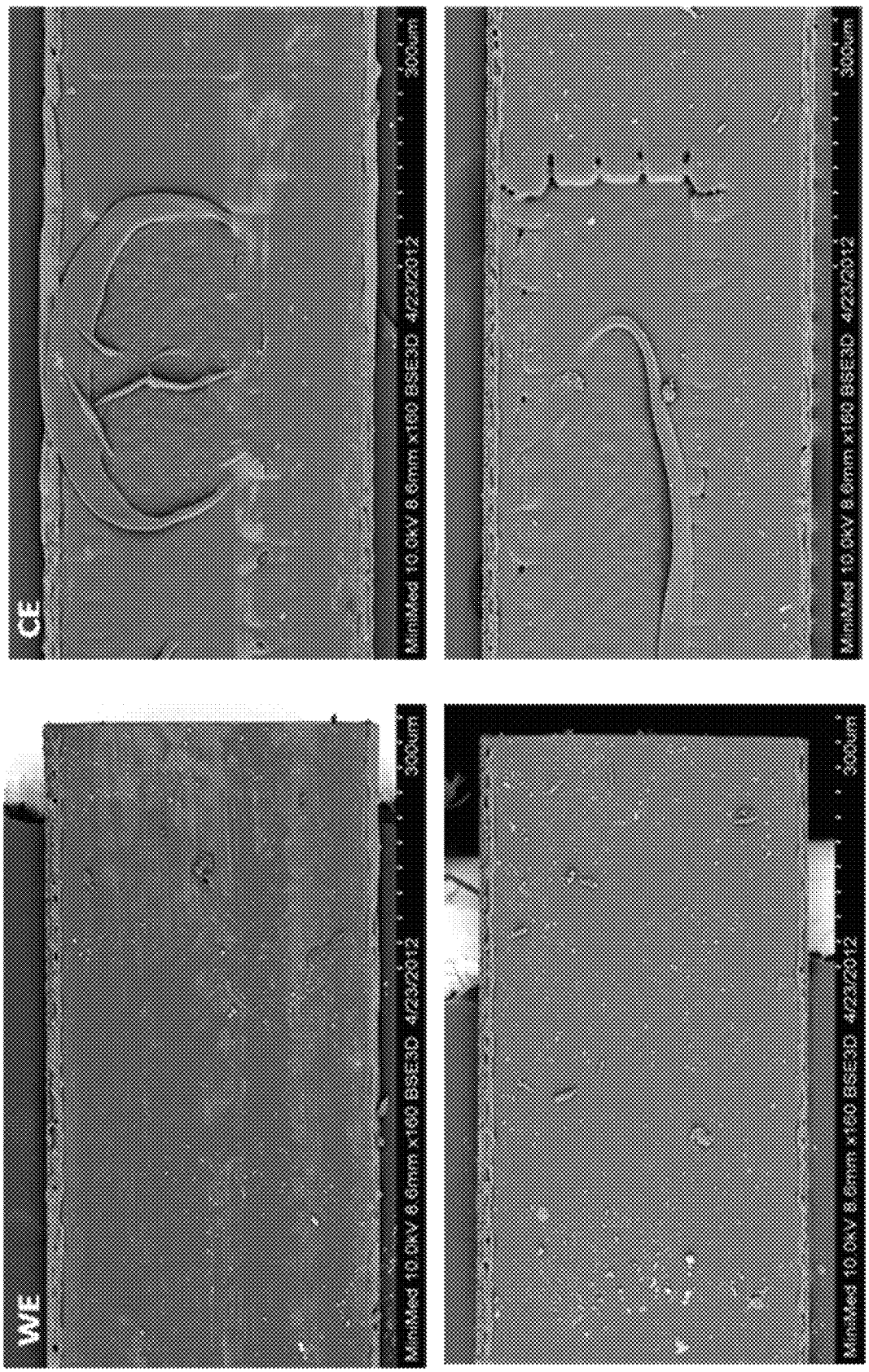
FIG. 20 provides photographs showing a comparison of pulse plated WEs with chemistry layers (left panels, showing no edge growth and no cracking) and counter electrodes (CEs) that were plated with continuous current, i.e. no pulses, (right panels, showing edge growth and cracking).

Yet another embodiment of the invention is an analyte sensor apparatus that includes a base substrate comprising a well that holds a platinum electrode composition formed using the pulse plating processes disclosed herein. In such embodiments, the structure of the platinum composition is formed to include a central planar region and an edge or ridge like region that surrounds the central planar region (see, e.g. FIG. 6). In such embodiments, the thickness or height of the platinum black layer at the edge is less than 2× the average thickness of the platinum black layer in the central planar region. In certain embodiments of the invention, the well comprises a lip that surrounds the well; and the edge region of the platinum black composition is below the lip of the well (see, e.g. FIG. 19). Typically in these embodiments, both the central planar region and the edge region of the electrode comprise platinum dendrites (see, e.g. FIGS. 6-8), and this layer of electrodeposited platinum black forms an electroactive surface of a working electrode in the sensor. Sensor embodiments of the invention typically include additional layers of material coated over the working electrode, for example an analyte sensing layer disposed over the working electrode, one that detectably alters the electrical current at the working electrode in the presence of an analyte as well as an analyte modulating layer disposed over the analyte sensing layer that modulates the diffusion of analyte therethrough.

In typical embodiments of the invention, the electrode is formed in a well of a base substrate comprising a dielectric material (e.g. a polyimide). Typically, the well includes a conductive material disposed at the bottom of the well (e.g. Au). Optionally the well in the base substrate is rectangular or circular. In certain embodiments of the invention, the base substrate comprises at least 10, 20 or 30 wells formed into a microarray. In typical sensor embodiments, a base substrate is formed so that it includes a well that comprises a lip surrounding the well. In certain processes disclosed herein, the platinum composition is pulse electrodeposited so that the edge region of the platinum black composition is below the lip of the well (see, e.g. FIG. 19). In addition, a variety of different electrically conductive elements can be disposed on the base substrate. In some embodiments of the invention, the base substrate comprises a plurality of reference electrodes, a plurality of working electrodes and a plurality of counter electrodes clustered together in units consisting essentially of one working electrode, one counter electrode and one reference electrode, and the clustered units are longitudinally distributed on the base substrate in a repeating pattern of units.

Embodiments of the invention include further elements designed for use with the sensor apparatuses that are disclosed herein, for example those that are designed to analyze electrical signal data obtained from pulse plated electrodes disposed on the base substrate. In some embodiments of the invention, the analyte sensor apparatus includes a processor and a computer-readable program code having instructions, which when executed, cause the processor to assess electrochemical signal data obtained from at least one working electrode and then compute analyte concentrations based upon the electrochemical signal data obtained from the working electrode. In certain embodiments of the invention, the processor compares electrochemical signal data obtained from multiple working electrodes in order to, for example, adapt different electrodes to sense different analytes, and/or to focus on different concentration ranges of a single analyte; and/or to identify or characterize spurious sensor signals (e.g. sensor noise, signals caused by interfering compounds and the like) so as to enhance the accuracy of the sensor readings.

In some embodiments of the invention, the base structure comprises a flexible yet rigid and flat structure suitable for use in photolithographic mask and etch processes. In this regard, the base structure typically includes at least one surface having a high degree of uniform flatness. Base structure materials can include, for example, metals such as stainless steel, aluminum and nickel titanium memory alloys (e.g. NITINOL) as well as polymeric/plastic materials such as delrin, etc. Base structure materials can be made from, or coated with, a dielectric material. In some embodiments, the base structure is non-rigid and can be a layer of film or insulation that is used as a substrate for patterning electrical elements (e.g. electrodes, traces and the like), for example plastics such as polyimides and the like. An initial step in the methods of the invention typically includes the formation of a base substrate of the sensor. Optionally, the planar sheet of material is formed and/or disposed on a support such as a glass or ceramic plate during sensor production (see, e.g. FIG. 12). The base structure can be disposed on a support (e.g. a glass plate) by any desired means, for example by controlled spin coating. Optionally, a base substrate layer of insulative material is formed on the support, typically by applying the base substrate material onto the support in liquid form and thereafter spinning the support to yield a base substrate structure that is thin and of a substantially uniform thickness. These steps can be repeated to build up a base substrate structure to a desired thickness. This can then be followed by a sequence of photolithographic and/or chemical mask and etch steps to form the electrically conductive components. In an illustrative form, the base substrate comprises a thin film sheet of insulative material, such as a polyimide substrate that is used to pattern electrical elements. The base substrate structure may comprise one or more of a variety of elements including, but not limited to, carbon, nitrogen, oxygen, silicon, sapphire, diamond, aluminum, copper, gallium, arsenic, lanthanum, neodymium, strontium, titanium, yttrium, or combinations thereof.

The methods of the invention include forming an electrically conductive layer on the base substrate that function as one or more sensing elements. Typically these sensing elements include electrodes, electrical conduits (e.g. traces and the like), contact pads and the like that are formed by one of the variety of methods known in the art such as photolithography, etching and rinsing to define the geometry of the active electrodes. The electrodes can then be made electrochemically active, for example by electrodeposition of Pt black for the working and counter electrode, and silver followed by silver chloride on the reference electrode. A sensor layer such as a analyte sensing enzyme layer can then be disposed on the sensing layer by electrochemical deposition or a method other than electrochemical deposition such as spin coating, followed by vapor crosslinking, for example with a dialdehyde (glutaraldehyde) or a carbodiimide.

In an exemplary embodiment of the invention, the base substrate is initially coated with a thin film conductive layer by electrode deposition, surface sputtering, or other suitable patterning or other process step. In one embodiment this conductive layer may be provided as a plurality of thin film conductive layers, such as an initial chrome-based layer suitable for chemical adhesion to a polyimide base substrate followed by subsequent formation of thin film gold-based and chrome-based layers in sequence. In alternative embodiments, other electrode layer conformations or materials can be used. The conductive layer is then covered, in accordance with conventional photolithographic techniques, with a selected photoresist coating, and a contact mask can be applied over the photoresist coating for suitable photoimaging. The contact mask typically includes one or more conductor trace patterns for appropriate exposure of the photoresist coating, followed by an etch step resulting in a plurality of conductive sensor traces remaining on the base substrate. In an illustrative sensor construction designed for use as a subcutaneous glucose sensor, each sensor trace can include two or three parallel sensor elements corresponding with two or three separate electrodes such as a working electrode, a counter electrode and a reference electrode.

Embodiments of the invention include methods of adding a plurality of materials to the surface(s) of the pulse plated electrode(s). One such embodiment of the invention is a method of making a sensor apparatus (e.g. a glucose sensor) for implantation within a mammal comprising the steps of: providing a base substrate; forming a conductive layer on the base substrate, wherein the conductive layer includes an electrode that has been electrodeposited via pulse plating (and optionally a working electrode, a reference electrode and a counter electrode); forming an analyte sensing layer on the conductive layer, wherein the analyte sensing layer includes a composition that can alter the electrical current at the electrode in the conductive layer in the presence of an analyte (e.g. glucose oxidase); optionally forming a protein layer over the analyte sensing layer; forming an adhesion promoting layer on the analyte sensing layer or the optional protein layer; forming an analyte modulating layer disposed on the adhesion promoting layer, wherein the analyte modulating layer includes a composition that modulates the diffusion of the analyte therethrough; and forming a cover layer disposed on at least a portion of the analyte modulating layer, wherein the cover layer further includes an aperture over at least a portion of the analyte modulating layer.

In the working embodiments of the invention that are disclosed herein, the analyte sensing layer comprises glucose oxidase. Optionally, the apparatus comprises an adhesion promoting layer disposed between the analyte sensing layer and the analyte modulating layer. In some embodiments of the invention, the analyte modulating layer comprises a hydrophilic comb-copolymer having a central chain and a plurality of side chains coupled to the central chain, wherein at least one side chain comprises a silicone moiety. Typically, the apparatus comprises a biocompatible material on an external surface that is adapted to contact biological tissues or fluids when implanted in vivo. In the working embodiments of the invention that are disclosed herein, the analyte sensor apparatus is an amperometric glucose sensor exhibits a highly desirable oxygen response profile. In such embodiments, the amperometric glucose sensor generates a first signal in a solution comprising 100 mg/dL glucose and 5% oxygen and a second signal in a solution comprising 100 mg/dL glucose and 0.1% oxygen (i.e. test conditions where the only substantive difference is the % oxygen), and the first signal and the second signal differ by less than 10%.

Additional functional coatings or cover layers can then be applied to an electrode or other senor element by any one of a wide variety of methods known in the art, such as spraying, dipping, etc. Some embodiments of the present invention include an analyte modulating layer deposited over an enzyme-containing layer that is disposed over a working electrode. In addition to its use in modulating the amount of analyte(s) that contacts the active sensor surface, by utilizing an analyte limiting membrane layer, the problem of sensor fouling by extraneous materials is also obviated. As is known in the art, the thickness of the analyte modulating membrane layer can influence the amount of analyte that reaches the active enzyme. Consequently, its application is typically carried out under defined processing conditions, and its dimensional thickness is closely controlled. Microfabrication of the underlying layers can be a factor which affects dimensional control over the analyte modulating membrane layer as well as the exact composition of the analyte limiting membrane layer material itself. In this regard, it has been discovered that several types of copolymers, for example, a copolymer of a siloxane and a nonsiloxane moiety, are particularly useful. These materials can be microdispensed or spin-coated to a controlled thickness. Their final architecture may also be designed by patterning and photolithographic techniques in conformity with the other discrete structures described herein.

In some embodiments of the invention, the sensor is made by methods which apply an analyte modulating layer that comprises a hydrophilic membrane coating which can regulate the amount of analyte that can contact the enzyme of the sensor layer. For example, a cover layer that is added to the glucose sensing elements of the invention can comprise a glucose limiting membrane, which regulates the amount of glucose that contacts glucose oxidase enzyme layer on an electrode. Such glucose limiting membranes can be made from a wide variety of materials known to be suitable for such purposes, e.g., silicones such as polydimethyl siloxane and the like, polyurethanes, cellulose acetates, Nafion, polyester sulfonic acids (e.g. Kodak AQ), hydrogels or any other membrane known to those skilled in the art that is suitable for such purposes. In certain embodiments of the invention, the analyte modulating layer comprises a hydrophilic polymer. In some embodiments of the invention, the analyte modulating layer comprises a linear polyurethane/polyurea polymer and/or a branched acrylate polymer; and/or a mixture of such polymers.

In some embodiments of the methods of invention, an adhesion promoter layer is disposed between a cover layer (e.g. an analyte modulating membrane layer) and a analyte sensing layer in order to facilitate their contact and is selected for its ability to increase the stability of the sensor apparatus. As noted herein, compositions of the adhesion promoter layer are selected to provide a number of desirable characteristics in addition to an ability to provide sensor stability. For example, some compositions for use in the adhesion promoter layer are selected to play a role in interference rejection as well as to control mass transfer of the desired analyte. The adhesion promoter layer can be made from any one of a wide variety of materials known in the art to facilitate the bonding between such layers and can be applied by any one of a wide variety of methods known in the art.

The finished sensors produced by such processes are typically quickly and easily removed from a support structure (if one is used), for example, by cutting along a line surrounding each sensor on the support structure. The cutting step can use methods typically used in this art such as those that include a UV laser cutting device that is used to cut through the base and cover layers and the functional coating layers along a line surrounding or circumscribing each sensor, typically in at least slight outward spaced relation from the conductive elements so that the sufficient interconnected base and cover layer material remains to seal the side edges of the finished sensor. Since the base substrate is typically not physically attached or only minimally adhered directly to the underlying support, the sensors can be lifted quickly and easily from the support structure, without significant further processing steps or potential damage due to stresses incurred by physically pulling or peeling attached sensors from the support structure. The support structure can thereafter be cleaned and reused, or otherwise discarded. The functional coating layer(s) can be applied either before or after other sensor components are removed from the support structure (e.g. by cutting).

Embodiments of the invention also include methods of sensing an analyte (e.g. glucose) within the body of a mammal (e.g. a diabetic patient), the method comprising implanting a analyte sensor embodiment disclosed herein into an in vivo environment and then sensing one or more electrical fluctuations such as alteration in current at the working electrode and correlating the alteration in current with the presence of the analyte, so that the analyte is sensed. Typically, this method comprises implanting a glucose sensor disclosed herein within the interstitial space of a diabetic individual, sensing an alteration in current at the working electrode in the presence of glucose; and then correlating the alteration in current with the presence of the glucose, so that glucose is sensed. While typical embodiments of the invention pertain to glucose sensors, the pulse plated sensor electrodes disclosed herein can be adapted for use with a wide variety of devices known in the art.

As discussed in detail below, embodiments of the invention include sensor systems comprising addition elements designed to facilitate sensing of an analyte. For example, in certain embodiments of the invention, the base material comprising the sensor electrodes is disposed within a housing (e.g. a lumen of a catheter) and/or associated with other components that facilitate analyte (e.g. glucose) sensing. One illustrative sensor system comprises a processor, a base comprising a first longitudinal member and a second longitudinal member, the first and second longitudinal members each comprising at least one electrode having an electrochemically reactive surface, wherein the electrochemically reactive surface generates an electrochemical signal that is assessed by the processor in the presence of an analyte; and a computer-readable program code having instructions, which when executed cause the processor to assess electrochemical signal data obtained from the electrodes; and compute an analyte presence or concentration based upon the electrochemical signal data obtained from the electrode. Embodiments of the invention described herein can also be adapted and implemented with amperometric sensor structures, for example those disclosed in U.S. Patent Application Publication Nos. 20070227907, 20400025238, 20110319734 and 20110152654, the contents of each of which are incorporated herein by reference.

B. Illustrative Analyte Sensor Constituents Used in Embodiments of the Invention The following disclosure provides examples of typical elements/constituents used in sensor embodiments of the invention. While these elements can be described as discrete units (e.g. layers), those of skill in the art understand that sensors can be designed to contain elements having a combination of some or all of the material properties and/or functions of the elements/constituents discussed below (e.g. an element that serves both as a supporting base constituent and/or a conductive constituent and/or a matrix for the analyte sensing constituent and which further functions as an electrode in the sensor). Those in the art understand that these thin film analyte sensors can be adapted for use in a number of sensor systems such as those described below.

Base Constituent

Figure 12:
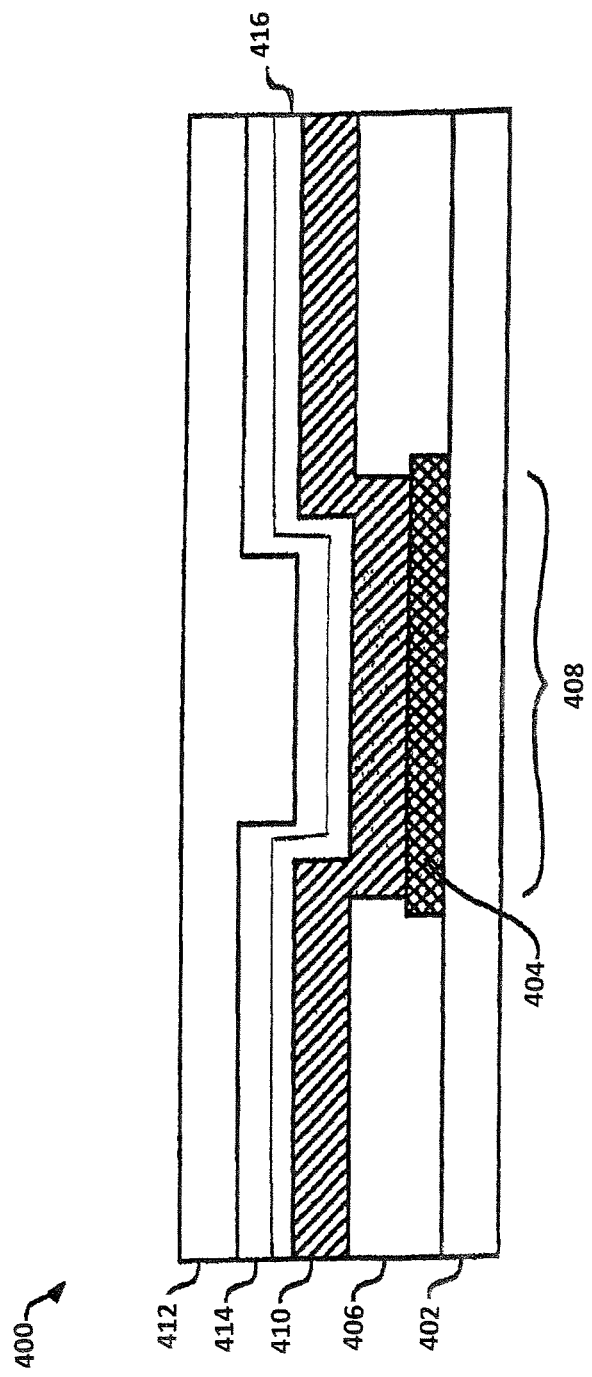
FIG. 12 shows illustrations of amperometric analyte sensors formed from a plurality of planar layered elements.
Figure 13:
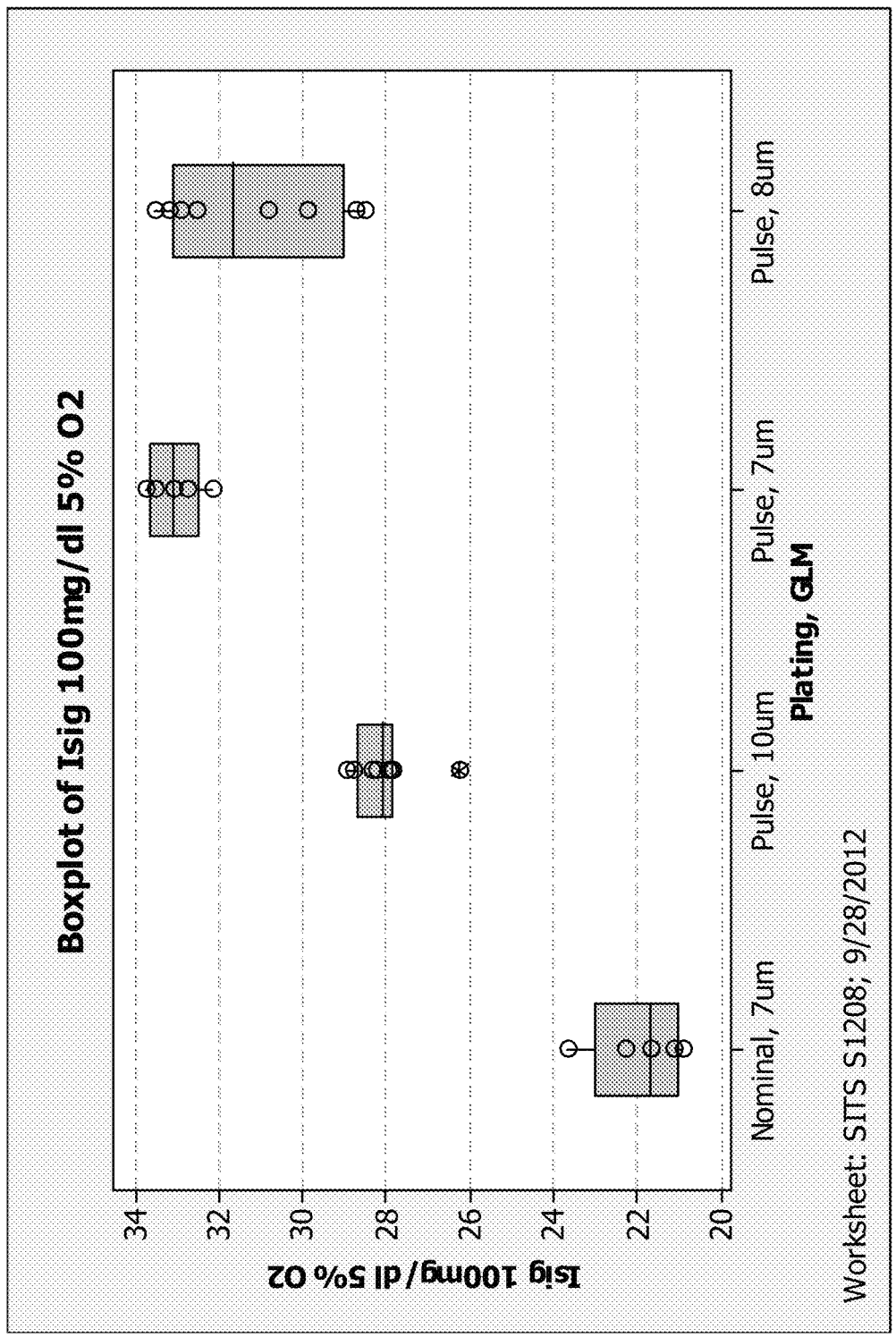
FIG. 13 provides a boxplot of Isig 100 mg/dl glucose, 5% $O_2$ data from electrodes made from various pulse plating methods and nonpulsed (nominal) plating methods.
Figure 14:
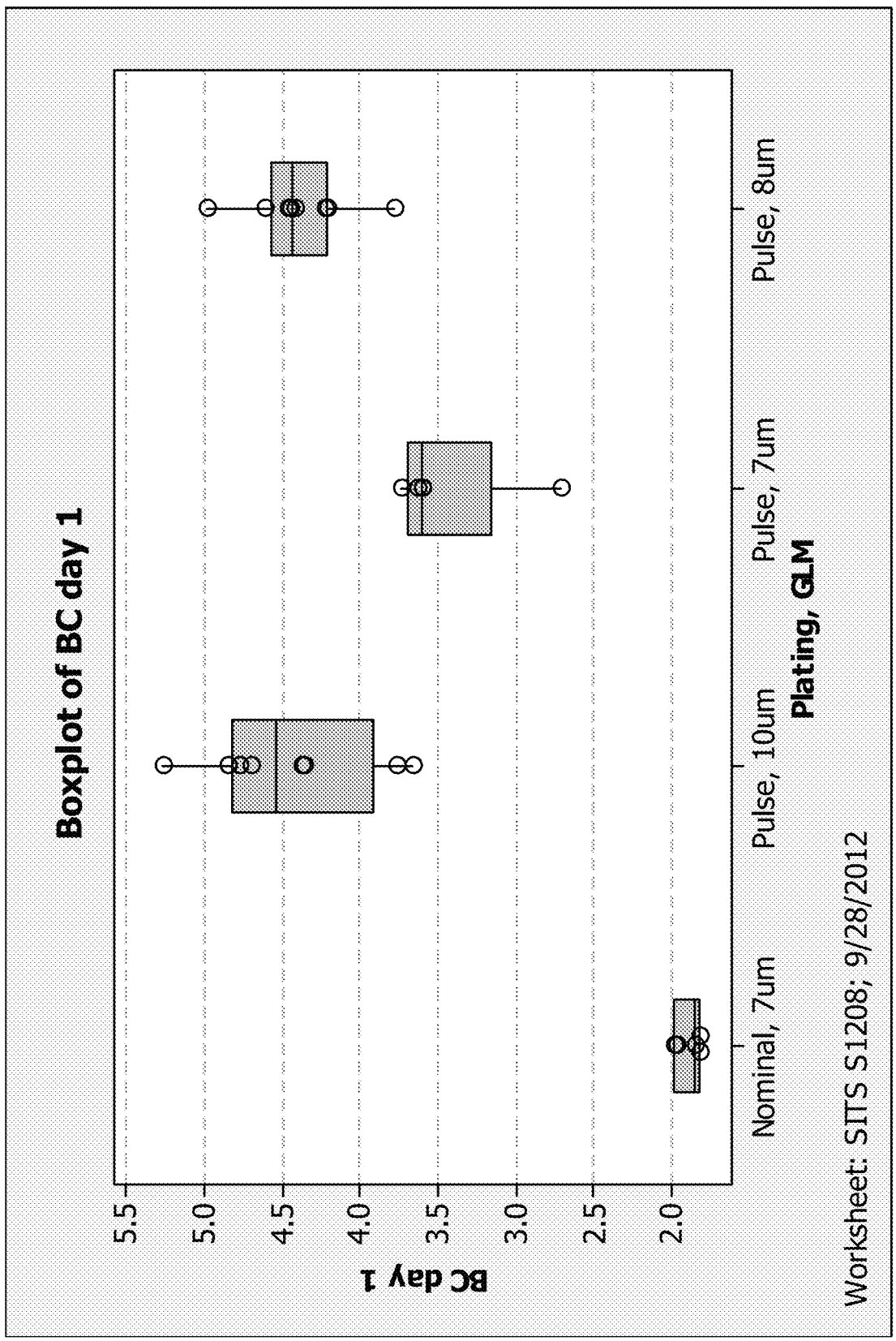
FIG. 14 provides a boxplot of background current sensor day 1 data from electrodes made from various pulse plating methods and nonpulsed (nominal) plating methods.

Sensors of the invention typically include a base constituent (see, e.g. element 402 in FIG. 12). The term "base constituent" is used herein according to art accepted terminology and refers to the constituent in the apparatus that typically provides a supporting matrix for the plurality of constituents that are stacked on top of one another and comprise the functioning sensor. In one form, the base constituent comprises a thin film sheet of insulative (e.g. electrically insulative and/or water impermeable) material. This base constituent can be made of a wide variety of materials having desirable qualities such as dielectric properties, water impermeability and hermeticity. Some materials include metallic, and/or ceramic and/or polymeric substrates or the like.

Conductive Constituent

The electrochemical sensors of the invention typically include a conductive constituent disposed upon the base constituent that includes at least one electrode for contacting an analyte or its byproduct (e.g. oxygen and/or hydrogen peroxide) to be assayed (see, e.g. element 404 in FIG. 12). The term "conductive constituent" is used herein according to art accepted terminology and refers to electrically conductive sensor elements such as electrodes, contact pads, traces and the like. An illustrative example of this is a conductive constituent that forms a working electrode that can measure an increase or decrease in current in response to exposure to a stimuli such as the change in the concentration of an analyte or its byproduct as compared to a reference electrode that does not experience the change in the concentration of the analyte, a coreactant (e.g. oxygen) used when the analyte interacts with a composition (e.g. the enzyme glucose oxidase) present in analyte sensing constituent 410 or a reaction product of this interaction (e.g. hydrogen peroxide). Illustrative examples of such elements include electrodes which are capable of producing variable detectable signals in the presence of variable concentrations of molecules such as hydrogen peroxide or oxygen.

In addition to the working electrode, the analyte sensors of the invention typically include a reference electrode or a combined reference and counter electrode (also termed a quasi-reference electrode or a counter/reference electrode). If the sensor does not have a counter/reference electrode then it may include a separate counter electrode, which may be made from the same or different materials as the working electrode. Typical sensors of the present invention have one or more working electrodes and one or more counter, reference, and/or counter/reference electrodes. One embodiment of the sensor of the present invention has two, three or four or more working electrodes. These working electrodes in the sensor may be integrally connected or they may be kept separate. Optionally, the electrodes can be disposed on a single surface or side of the sensor structure. Alternatively, the electrodes can be disposed on a multiple surfaces or sides of the sensor structure. In certain embodiments of the invention, the reactive surfaces of the electrodes are of different relative areas/sizes, for example a 1× reference electrode, a 3.2× working electrode and a 6.3× counter electrode.

Interference Rejection Constituent

The electrochemical sensors of the invention optionally include an interference rejection constituent disposed between the surface of the electrode and the environment to be assayed. In particular, certain sensor embodiments rely on the oxidation and/or reduction of hydrogen peroxide generated by enzymatic reactions on the surface of a working electrode at a constant potential applied. Because amperometric detection based on direct oxidation of hydrogen peroxide requires a relatively high oxidation potential, sensors employing this detection scheme may suffer interference from oxidizable species that are present in biological fluids such as ascorbic acid, uric acid and acetaminophen. In this context, the term "interference rejection constituent" is used herein according to art accepted terminology and refers to a coating or membrane in the sensor that functions to inhibit spurious signals generated by such oxidizable species which interfere with the detection of the signal generated by the analyte to be sensed. Certain interference rejection constituents function via size exclusion (e.g. by excluding interfering species of a specific size). Examples of interference rejection constituents include one or more layers or coatings of compounds such as hydrophilic polyurethanes, cellulose acetate (including cellulose acetate incorporating agents such as poly(ethylene glycol), polyethersulfones, polytetra-fluoroethylenes, the perfluoronated ionomer Nafion™, polyphenylenediamine, epoxy and the like.

Analyte Sensing Constituent

The electrochemical sensors of the invention include an analyte sensing constituent disposed on the electrodes of the sensor (see, e.g. element 410 in FIG. 12). The term "analyte sensing constituent" is used herein according to art accepted terminology and refers to a constituent comprising a material that is capable of recognizing or reacting with an analyte whose presence is to be detected by the analyte sensor apparatus. Typically, this material in the analyte sensing constituent produces a detectable signal after interacting with the analyte to be sensed, typically via the electrodes of the conductive constituent. In this regard, the analyte sensing constituent and the electrodes of the conductive constituent work in combination to produce the electrical signal that is read by an apparatus associated with the analyte sensor. Typically, the analyte sensing constituent comprises an oxidoreductase enzyme capable of reacting with and/or producing a molecule whose change in concentration can be measured by measuring the change in the current at an electrode of the conductive constituent (e.g. oxygen and/or hydrogen peroxide), for example the enzyme glucose oxidase. An enzyme capable of producing a molecule such as hydrogen peroxide can be disposed on the electrodes according to a number of processes known in the art. The analyte sensing constituent can coat all or a portion of the various electrodes of the sensor. In this context, the analyte sensing constituent may coat the electrodes to an equivalent degree. Alternatively, the analyte sensing constituent may coat different electrodes to different degrees, with for example the coated surface of the working electrode being larger than the coated surface of the counter and/or reference electrode.

Typical sensor embodiments of this element of the invention utilize an enzyme (e.g. glucose oxidase) that has been combined with a second protein (e.g. albumin) in a fixed ratio (e.g. one that is typically optimized for glucose oxidase stabilizing properties) and then applied on the surface of an electrode to form a thin enzyme constituent. In a typical embodiment, the analyte sensing constituent comprises a GOx and HSA mixture. In a typical embodiment of an analyte sensing constituent having GOx, the GOx reacts with glucose present in the sensing environment (e.g. the body of a mammal) and generates hydrogen peroxide.

As noted above, the enzyme and the second protein (e.g. an albumin) are typically treated to form a crosslinked matrix (e.g. by adding a cross-linking agent to the protein mixture). As is known in the art, crosslinking conditions may be manipulated to modulate factors such as the retained biological activity of the enzyme, its mechanical and/or operational stability. Illustrative crosslinking procedures are described in U.S. patent application Ser. No. 10/335,506 and PCT publication WO 03/035891 which are incorporated herein by reference. For example, an amine cross-linking reagent, such as, but not limited to, glutaraldehyde, can be added to the protein mixture. The addition of a cross-linking reagent to the protein mixture creates a protein paste. The concentration of the cross-linking reagent to be added may vary according to the concentration of the protein mixture. While glutaraldehyde is an illustrative crosslinking reagent, other cross-linking reagents may also be used or may be used in place of glutaraldehyde. Other suitable cross-linkers also may be used, as will be evident to those skilled in the art.

As noted above, in some embodiments of the invention, the analyte sensing constituent includes an agent (e.g. glucose oxidase) capable of producing a signal (e.g. a change in oxygen and/or hydrogen peroxide concentrations) that can be sensed by the electrically conductive elements (e.g.

electrodes which sense changes in oxygen and/or hydrogen peroxide concentrations). However, other useful analyte sensing constituents can be formed from any composition that is capable of producing a detectable signal that can be sensed by the electrically conductive elements after interacting with a target analyte whose presence is to be detected. In some embodiments, the composition comprises an enzyme that modulates hydrogen peroxide concentrations upon reaction with an analyte to be sensed. Alternatively, the composition comprises an enzyme that modulates oxygen concentrations upon reaction with an analyte to be sensed. In this context, a wide variety of enzymes that either use or produce hydrogen peroxide and/or oxygen in a reaction with a physiological analyte are known in the art and these enzymes can be readily incorporated into the analyte sensing constituent composition. A variety of other enzymes known in the art can produce and/or utilize compounds whose modulation can be detected by electrically conductive elements such as the electrodes that are incorporated into the sensor designs described herein. Such enzymes include for example, enzymes specifically described in Table 1, pages 15-29 and/or Table 18, pages 111-112 of Protein Immobilization: Fundamentals and Applications (Bioprocess Technology, Vol 14) by Richard F. Taylor (Editor) Publisher: Marcel Dekker; Jan. 7, 1991) the entire contents of which are incorporated herein by reference.

Protein Constituent

The electrochemical sensors of the invention optionally include a protein constituent disposed between the analyte sensing constituent and the analyte modulating constituent (see, e.g. element 416 in FIG. 12). The term "protein constituent" is used herein according to art accepted terminology and refers to constituent containing a carrier protein or the like that is selected for compatibility with the analyte sensing constituent and/or the analyte modulating constituent. In typical embodiments, the protein constituent comprises an albumin such as human serum albumin. The HSA concentration may vary between about 0.5%-30% (w/v). Typically the HSA concentration is about 1-10% w/v, and most typically is about 5% w/v. In alternative embodiments of the invention, collagen or BSA or other structural proteins used in these contexts can be used instead of or in addition to HSA. This constituent is typically crosslinked on the analyte sensing constituent according to art accepted protocols.

Adhesion Promoting Constituent

The electrochemical sensors of the invention can include one or more adhesion promoting (AP) constituents (see, e.g. element 414 in FIG. 12). The term "adhesion promoting constituent" is used herein according to art accepted terminology and refers to a constituent that includes materials selected for their ability to promote adhesion between adjoining constituents in the sensor. Typically, the adhesion promoting constituent is disposed between the analyte sensing constituent and the analyte modulating constituent. Typically, the adhesion promoting constituent is disposed between the optional protein constituent and the analyte modulating constituent. The adhesion promoter constituent can be made from any one of a wide variety of materials known in the art to facilitate the bonding between such constituents and can be applied by any one of a wide variety of methods known in the art. Typically, the adhesion promoter constituent comprises a silane compound such as 3-aminopropyltrimethoxysilane.

Analyte Modulating Constituent

The electrochemical sensors of the invention include an analyte modulating constituent disposed on the sensor (see, e.g. element 412 in FIG. 12). The term "analyte modulating constituent" is used herein according to art accepted terminology and refers to a constituent that typically forms a membrane on the sensor that operates to modulate the diffusion of one or more analytes, such as glucose, through the constituent. In certain embodiments of the invention, the analyte modulating constituent is an analyte-limiting membrane which operates to prevent or restrict the diffusion of one or more analytes, such as glucose, through the constituents. In other embodiments of the invention, the analyte-modulating constituent operates to facilitate the diffusion of one or more analytes, through the constituents. Optionally, such analyte modulating constituents can be formed to prevent or restrict the diffusion of one type of molecule through the constituent (e.g. glucose), while at the same time allowing or even facilitating the diffusion of other types of molecules through the constituent (e.g. $O_2$).

With respect to glucose sensors, in known enzyme electrodes, glucose and oxygen from blood, as well as some interferants, such as ascorbic acid and uric acid, diffuse through a primary membrane of the sensor. As the glucose, oxygen and interferants reach the analyte sensing constituent, an enzyme, such as glucose oxidase, catalyzes the conversion of glucose to hydrogen peroxide and gluconolactone. The hydrogen peroxide may diffuse back through the analyte modulating constituent, or it may diffuse to an electrode where it can be reacted to form oxygen and a proton to produce a current that is proportional to the glucose concentration. The analyte modulating sensor membrane assembly serves several functions, including selectively allowing the passage of glucose therethrough (see, e.g. U.S. Patent Application No. 2011-0152654).

Cover Constituent

The electrochemical sensors of the invention include one or more cover constituents, which are typically electrically insulating protective constituents (see, e.g. element 406 in FIG. 12). Typically, such cover constituents can be in the form of a coating, sheath or tube and are disposed on at least a portion of the analyte modulating constituent. Acceptable polymer coatings for use as the insulating protective cover constituent can include, but are not limited to, non-toxic biocompatible polymers such as silicone compounds, polyimides, biocompatible solder masks, epoxy acrylate copolymers, or the like. Further, these coatings can be photoimageable to facilitate photolithographic forming of apertures through to the conductive constituent. A typical cover constituent comprises spun on silicone. As is known in the art, this constituent can be a commercially available RTV (room temperature vulcanized) silicone composition. A typical chemistry in this context is polydimethyl siloxane (acetoxy based).

Illustrative Sensor Stacks

An embodiment of the invention having a layered stack of constituents is shown in FIG. 12. FIG. 12 illustrates a cross-section of a typical sensor embodiment 400 of the present invention that includes constituents discussed above. This sensor embodiment is formed from a plurality of components that are typically in the form of layers of various conductive and non-conductive constituents disposed on each other according to art accepted methods and/or the specific methods of the invention disclosed herein. The components of the sensor are typically characterized herein as layers because, for example, it allows for a facile characterization of the sensor structure shown in FIG. 12. Artisans will understand however, that in certain embodiments of the invention, the sensor constituents are combined such that multiple constituents form one or more heterogeneous layers. In this context, those of skill in the art understand that the ordering of the layered constituents can be altered in various embodiments of the invention.

The embodiment shown in FIG. 12 includes a base substrate layer 402 to support the sensor 400. The base substrate layer 402 can be made of a material such as a metal and/or a ceramic and/or a polymeric substrate, which may be self-supporting or further supported by another material as is known in the art. Embodiments of the invention include a conductive layer 404 which is disposed on and/or combined with the base substrate layer 402. Typically, the conductive layer 404 comprises one or more electrically conductive elements that function as electrodes. An operating sensor 400 typically includes a plurality of electrodes such as a working electrode, a counter electrode and a reference electrode. Other embodiments may also include a plurality of working and/or counter and/or reference electrodes and/or one or more electrodes that performs multiple functions, for example one that functions as both as a reference and a counter electrode.

As discussed in detail below, the base layer 402 and/or conductive layer 404 can be generated using many known techniques and materials. In certain embodiments of the invention, the electrical circuit of the sensor is defined by etching the disposed conductive layer 404 into a desired pattern of conductive paths. A typical electrical circuit for the sensor 400 comprises two or more adjacent conductive paths with regions at a proximal end to form contact pads and regions at a distal end to form sensor electrodes. An electrically insulating cover layer 406 such as a polymer coating can be disposed on portions of the sensor 400. Acceptable polymer coatings for use as the insulating protective cover layer 406 can include, but are not limited to, non-toxic biocompatible polymers such as silicone compounds, polyimides, biocompatible solder masks, epoxy acrylate copolymers, or the like. In the sensors of the present invention, one or more exposed regions or apertures 408 can be made through the cover layer 406 to open the conductive layer 404 to the external environment and to, for example, allow an analyte such as glucose to permeate the layers of the sensor and be sensed by the sensing elements. Apertures 408 can be formed by a number of techniques, including laser ablation, tape masking, chemical milling or etching or photolithographic development or the like. In certain embodiments of the invention, during manufacture, a secondary photoresist can also be applied to the protective layer 406 to define the regions of the protective layer to be removed to form the aperture(s) 408. The exposed electrodes and/or contact pads can also undergo secondary processing (e.g. through the apertures 408), such as additional plating processing, to prepare the surfaces and/or strengthen the conductive regions.

In the sensor configuration shown in FIG. 12, an analyte sensing layer 410 is disposed on one or more of the exposed electrodes of the conductive layer 404. Typically, the analyte sensing layer 410 is an enzyme layer. Most typically, the analyte sensing layer 410 comprises an enzyme capable of producing and/or utilizing oxygen and/or hydrogen peroxide, for example the enzyme glucose oxidase. Optionally, the enzyme in the analyte sensing layer is combined with a second carrier protein such as human serum albumin, bovine serum albumin or the like. In an illustrative embodiment, an oxidoreductase enzyme such as glucose oxidase in the analyte sensing layer 410 reacts with glucose to produce hydrogen peroxide, a compound which then modulates a current at an electrode. As this modulation of current depends on the concentration of hydrogen peroxide, and the concentration of hydrogen peroxide correlates to the concentration of glucose, the concentration of glucose can be determined by monitoring this modulation in the current. In a specific embodiment of the invention, the hydrogen peroxide is oxidized at a working electrode which is an anode (also termed herein the anodic working electrode), with the resulting current being proportional to the hydrogen peroxide concentration. Such modulations in the current caused by changing hydrogen peroxide concentrations can be monitored by any one of a variety of sensor detector apparatuses such as a universal sensor amperometric biosensor detector or one of the variety of similar devices known in the art such as glucose monitoring devices produced by Medtronic Diabetes.

In embodiments of the invention, the analyte sensing layer 410 can be applied over portions of the conductive layer or over the entire region of the conductive layer. Typically the analyte sensing layer 410 is disposed on the working electrode which can be the anode or the cathode. Optionally, the analyte sensing layer 410 is also disposed on a counter and/or reference electrode. Methods for generating a thin analyte sensing layer 410 include brushing the layer onto a substrate (e.g. the reactive surface of a platinum black electrode), as well as spin coating processes, dip and dry processes, low shear spraying processes, ink-jet printing processes, silk screen processes and the like. In certain embodiments of the invention, brushing is used to: (1) allow for a precise localization of the layer; and (2) push the layer deep into the architecture of the reactive surface of an electrode (e.g. platinum black produced by an electrodeposition process).

Typically, the analyte sensing layer 410 is coated and or disposed next to one or more additional layers. Optionally, the one or more additional layers includes a protein layer 416 disposed upon the analyte sensing layer 410. Typically, the protein layer 416 comprises a protein such as human serum albumin, bovine serum albumin or the like. Typically, the protein layer 416 comprises human serum albumin. In some embodiments of the invention, an additional layer includes an analyte modulating layer 412 that is disposed above the analyte sensing layer 410 to regulate analyte contact with the analyte sensing layer 410. For example, the analyte modulating membrane layer 412 can comprise a glucose limiting membrane, which regulates the amount of glucose that contacts an enzyme such as glucose oxidase that is present in the analyte sensing layer. Such glucose limiting membranes can be made from a wide variety of materials known to be suitable for such purposes, e.g., silicone compounds such as polydimethyl siloxanes, polyurethanes, polyurea cellulose acetates, Nafion, polyester sulfonic acids (e.g. Kodak AQ), hydrogels or any other suitable hydrophilic membranes known to those skilled in the art.

In certain embodiments of the invention, an adhesion promoter layer 414 is disposed between the analyte modulating layer 412 and the analyte sensing layer 410 as shown in FIG. 12 in order to facilitate their contact and/or adhesion. In a specific embodiment of the invention, an adhesion promoter layer 414 is disposed between the analyte modulating layer 412 and the protein layer 416 as shown in FIG. 12 in order to facilitate their contact and/or adhesion. The adhesion promoter layer 414 can be made from any one of a wide variety of materials known in the art to facilitate the bonding between such layers. Typically, the adhesion promoter layer 414 comprises a silane compound. In alternative embodiments, protein or like molecules in the analyte sensing layer 410 can be sufficiently crosslinked or otherwise prepared to allow the analyte modulating membrane layer 412 to be disposed in direct contact with the analyte sensing layer 410 in the absence of an adhesion promoter layer 414.

C. Typical System Embodiments of the Invention

A specific illustrative system embodiment consists of a glucose sensor comprising a pulse plated platinum electrode composition as disclosed herein, a transmitter and receiver and a glucose meter. In this system, radio signals from the transmitter can be sent to the pump receiver at regular time periods (e.g. every 5 minutes) to provide real-time sensor glucose (SG) values. Values/graphs can be displayed on a monitor of the pump receiver so that a user can self monitor blood glucose and deliver insulin using their own insulin pump. Typically the sensor systems disclosed herein can communicate with other medical devices/systems via a wired or wireless connection. Wireless communication can include for example the reception of emitted radiation signals as occurs with the transmission of signals via RF telemetry, infrared transmissions, optical transmission, sonic and ultrasonic transmissions and the like. Optionally, the device is an integral part of a medication infusion pump (e.g. an insulin pump). Typically in such devices, the physiological characteristic values include a plurality of measurements of blood glucose.

Figure 10:
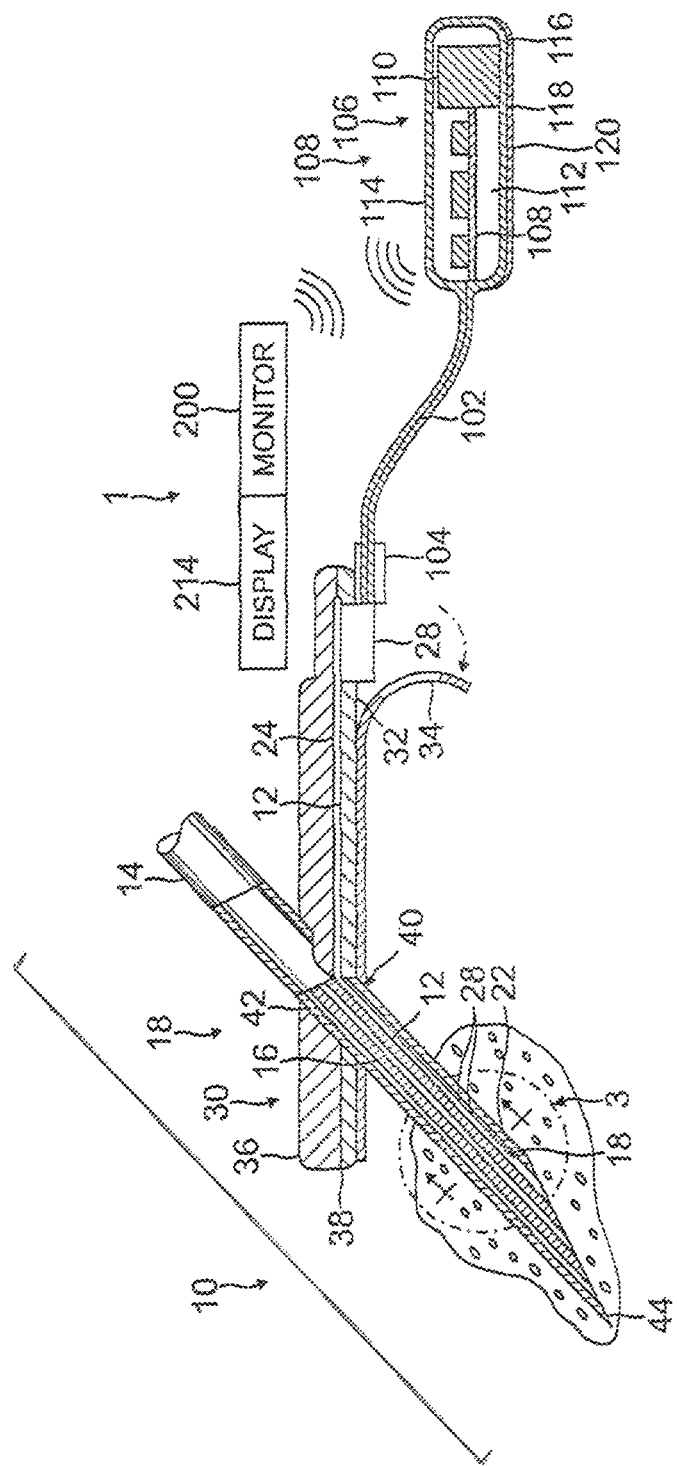
FIG. 10 provides a perspective view illustrating one type of subcutaneous sensor insertion set, a telemetered characteristic monitor transmitter device, and a data receiving device, elements that can be adapted for use with embodiments of the invention.

FIG. 10 provides a perspective view of one generalized embodiment of subcutaneous sensor insertion system that can be adapted for use with the sensor electrodes disclosed herein and a block diagram of a sensor electronics device according to one illustrative embodiment of the invention. Additional elements typically used with such sensor system embodiments are disclosed for example in U.S. Patent Application No. 20070163894, the contents of which are incorporated by reference. FIG. 10 provides a perspective view of a telemetered characteristic monitor system 1, including a subcutaneous sensor set 10 provided for subcutaneous placement of an active portion of a flexible sensor 12, or the like, at a selected site in the body of a user. The subcutaneous or percutaneous portion of the sensor set 10 includes a hollow, slotted insertion needle 14 having a sharpened tip 44, and a cannula 16. Inside the cannula 16 is a sensing portion 18 of the sensor 12 to expose one or more sensor electrodes 20 to the user's bodily fluids through a window 22 formed in the cannula 16. The base is designed so that the sensing portion 18 is joined to a connection portion 24 that terminates in conductive contact pads, or the like, which are also exposed through one of the insulative layers. The connection portion 24 and the contact pads are generally adapted for a direct wired electrical connection to a suitable monitor 200 coupled to a display 214 for monitoring a user's condition in response to signals derived from the sensor electrodes 20. The connection portion 24 may be conveniently connected electrically to the monitor 200 or a characteristic monitor transmitter 200 by a connector block 28 (or the like) as shown and described in U.S. Pat. No. 5,482,473, entitled FLEX CIRCUIT CONNECTOR, which is incorporated by reference.

As shown in FIG. 10, in accordance with embodiments of the present invention, subcutaneous sensor set 10 may be configured or formed to work with either a wired or a wireless characteristic monitor system. The proximal part of the sensor 12 is mounted in a mounting base 30 adapted for placement onto the skin of a user. The mounting base 30 can be a pad having an underside surface coated with a suitable pressure sensitive adhesive layer 32, with a peel-off paper strip 34 normally provided to cover and protect the adhesive layer 32, until the sensor set 10 is ready for use. The mounting base 30 includes upper and lower layers 36 and 38, with the connection portion 24 of the flexible sensor 12 being sandwiched between the layers 36 and 38. The connection portion 24 has a forward section joined to the active sensing portion 18 of the sensor 12, which is folded angularly to extend downwardly through a bore 40 formed in the lower base layer 38. Optionally, the adhesive layer 32 (or another portion of the apparatus in contact with in vivo tissue) includes an anti-inflammatory agent to reduce an inflammatory response and/or anti-bacterial agent to reduce the chance of infection. The insertion needle 14 is adapted for slide-fit reception through a needle port 42 formed in the upper base layer 36 and through the lower bore 40 in the lower base layer 38. After insertion, the insertion needle 14 is withdrawn to leave the cannula 16 with the sensing portion 18 and the sensor electrodes 20 in place at the selected insertion site. In this embodiment, the telemetered characteristic monitor transmitter 200 is coupled to a sensor set 10 by a cable 102 through a connector 104 that is electrically coupled to the connector block 28 of the connection portion 24 of the sensor set 10.

In the embodiment shown in FIG. 10, the telemetered characteristic monitor 200 includes a housing 106 that supports a printed circuit board 108, batteries 110, antenna 112, and the cable 102 with the connector 104. In some embodiments, the housing 106 is formed from an upper case 114 and a lower case 116 that are sealed with an ultrasonic weld to form a waterproof (or resistant) seal to permit cleaning by immersion (or swabbing) with water, cleaners, alcohol or the like. In some embodiments, the upper and lower case 114 and 116 are formed from a medical grade plastic. However, in alternative embodiments, the upper case 114 and lower case 116 may be connected together by other methods, such as snap fits, sealing rings, RTV (silicone sealant) and bonded together, or the like, or formed from other materials, such as metal, composites, ceramics, or the like. In other embodiments, the separate case can be eliminated and the assembly is simply potted in epoxy or other moldable materials that is compatible with the electronics and reasonably moisture resistant. As shown, the lower case 116 may have an underside surface coated with a suitable pressure sensitive adhesive layer 118, with a peel-off paper strip 120 normally provided to cover and protect the adhesive layer 118, until the sensor set telemetered characteristic monitor transmitter 200 is ready for use.

In the illustrative embodiment shown in FIG. 10, the subcutaneous sensor set 10 facilitates accurate placement of a flexible thin film electrochemical sensor 12 of the type used for monitoring specific blood parameters representative of a user's condition. The sensor 12 monitors glucose levels in the body, and may be used in conjunction with automated or semi-automated medication infusion pumps of the external or implantable type as described in U.S. Pat. Nos. 4,562,751; 4,678,408; 4,685,903 or 4,573,994, to control delivery of insulin to a diabetic patient.

In the illustrative embodiment shown in FIG. 10, the sensor electrodes 10 may be used in a variety of sensing applications and may be configured in a variety of positions on a base structure and further be formed to include materials that allow a wide variety of functions. For example, the sensor electrodes 10 may be used in physiological parameter sensing applications in which some type of biomolecule is used as a catalytic agent. For example, the sensor electrodes 10 may be used in a glucose and oxygen sensor having a glucose oxidase enzyme catalyzing a reaction with the sensor electrodes 20. The sensor electrodes 10, along with a biomolecule or some other catalytic agent, may be placed in a human body in a vascular or non-vascular environment. For example, the sensor electrodes 20 and biomolecule may be placed in a vein and be subjected to a blood stream, or may be placed in a subcutaneous or peritoneal region of the human body.

In the embodiment of the invention shown in FIG. 10, the monitor of sensor signals 200 may also be referred to as a sensor electronics device 200. The monitor 200 may include a power source, a sensor interface, processing electronics (i.e. a processor), and data formatting electronics. The monitor 200 may be coupled to the sensor set 10 by a cable 102 through a connector that is electrically coupled to the connector block 28 of the connection portion 24. In an alternative embodiment, the cable may be omitted. In this embodiment of the invention, the monitor 200 may include an appropriate connector for direct connection to the connection portion 104 of the sensor set 10. The sensor set 10 may be modified to have the connector portion 104 positioned at a different location, e.g., on top of the sensor set to facilitate placement of the monitor 200 over the sensor set.

As noted above, embodiments of the sensor elements and sensors can be operatively coupled to a variety of other system elements typically used with analyte sensors (e.g. structural elements such as piercing members, insertion sets and the like as well as electronic components such as processors, monitors, medication infusion pumps and the like), for example to adapt them for use in various contexts (e.g. implantation within a mammal). One embodiment of the invention includes a method of monitoring a physiological characteristic of a user using an embodiment of the invention that includes an input element capable of receiving a signal from a sensor that is based on a sensed physiological characteristic value of the user, and a processor for analyzing the received signal. In typical embodiments of the invention, the processor determines a dynamic behavior of the physiological characteristic value and provides an observable indicator based upon the dynamic behavior of the physiological characteristic value so determined. In some embodiments, the physiological characteristic value is a measure of the concentration of blood glucose in the user. In other embodiments, the process of analyzing the received signal and determining a dynamic behavior includes repeatedly measuring the physiological characteristic value to obtain a series of physiological characteristic values in order to, for example, incorporate comparative redundancies into a sensor apparatus in a manner designed to provide confirmatory information on sensor function, analyte concentration measurements, the presence of interferences and the like.

Figure 11:
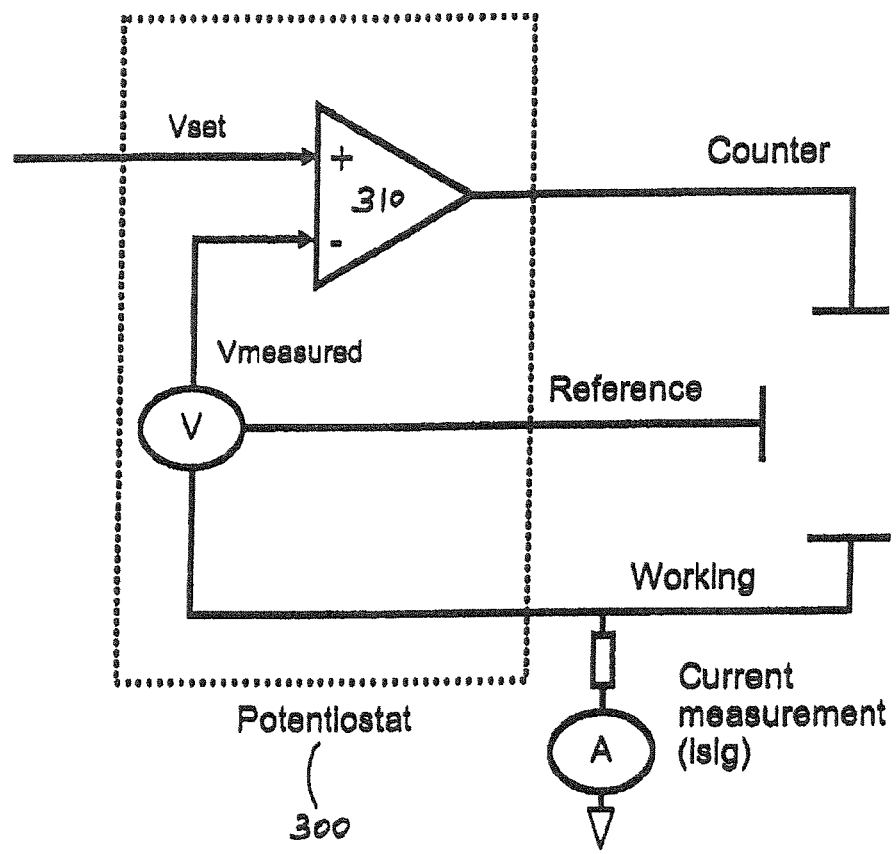
FIG. 11 shows a schematic of a potentiostat that may be used to measure current in embodiments of the present invention.

FIG. 11 shows a schematic of a potentiostat that may be used to measure current in embodiments of the present invention. As shown in FIG. 11, a potentiostat 300 may include an op amp 310 that is connected in an electrical circuit so as to have two inputs: Vset and Vmeasured. As shown, Vmeasured is the measured value of the voltage between a reference electrode and a working electrode. Vset, on the other hand, is the optimally desired voltage across the working and reference electrodes. The current between the counter and reference electrode is measured, creating a current measurement (Isig) that is output from the potentiostat.

Embodiments of the invention include devices which process display data from measurements of a sensed physiological characteristic (e.g. blood glucose concentrations) in a manner and format tailored to allow a user of the device to easily monitor and, if necessary, modulate the physiological status of that characteristic (e.g. modulation of blood glucose concentrations via insulin administration). An illustrative embodiment of the invention is a device comprising a sensor input capable of receiving a signal from a sensor, the signal being based on a sensed physiological characteristic value of a user; a memory for storing a plurality of measurements of the sensed physiological characteristic value of the user from the received signal from the sensor; and a display for presenting a text and/or graphical representation of the plurality of measurements of the sensed physiological characteristic value (e.g. text, a line graph or the like, a bar graph or the like, a grid pattern or the like or a combination thereof). Typically, the graphical representation displays real time measurements of the sensed physiological characteristic value. Such devices can be used in a variety of contexts, for example in combination with other medical apparatuses. In some embodiments of the invention, the device is used in combination with at least one other medical device (e.g. a glucose sensor).

An illustrative system embodiment consists of a glucose sensor, a transmitter and pump receiver and a glucose meter. In this system, radio signals from the transmitter can be sent to the pump receiver every 5 minutes to provide real-time sensor glucose (SG) values. Values/graphs are displayed on a monitor of the pump receiver so that a user can self monitor blood glucose and deliver insulin using their own insulin pump. Typically, an embodiment of device disclosed herein communicates with a second medical device via a wired or wireless connection. Wireless communication can include for example the reception of emitted radiation signals as occurs with the transmission of signals via RF telemetry, infrared transmissions, optical transmission, sonic and ultrasonic transmissions and the like. Optionally, the device is an integral part of a medication infusion pump (e.g. an insulin pump). Typically in such devices, the physiological characteristic values include a plurality of measurements of blood glucose.

While the analyte sensor and sensor systems disclosed herein are typically designed to be implantable within the body of a mammal, the inventions disclosed herein are not limited to any particular environment and can instead be used in a wide variety of contexts, for example for the analysis of most in vivo and in vitro liquid samples including biological fluids such as interstitial fluids, whole-blood, lymph, plasma, serum, saliva, urine, stool, perspiration, mucus, tears, cerebrospinal fluid, nasal secretion, cervical or vaginal secretion, semen, pleural fluid, amniotic fluid, peritoneal fluid, middle ear fluid, joint fluid, gastric aspirate or the like. In addition, solid or desiccated samples may be dissolved in an appropriate solvent to provide a liquid mixture suitable for analysis.

EXAMPLES

Example 1: Pulse Plating Conditions that Produce High Surface Area Ratios and Low Edge Growth The surface area ratio (SAR) is the ratio between real surface area and geometric area of the electrode. The active (or real) surface area determines the catalytic activity of plated electrodes. The active surface area of the platinum-working electrodes can be measured using the cyclic voltammetry method combined with hydrogen adsorption. In this context, various determinations of Pt surface area are well known in the art, see, e.g. Rodriguez et al., J. Chem. Educ., 2000, 77 (9), p 1195.

Certain electrodes made with platinum plating techniques that do not utilize current pulses can have a desirable SAR (e.g. one of around 300) but also an edge growth at the distal corners of about 15 to 20 μm. A goal of the pulsed current plating processes disclosed herein is to achieve SAR close to 300 while simultaneously reducing edge growth. "Edge growth": as discussed in the examples below is the height of platinum black on the distal corners of working electrodes measured from the level of surrounding polyimide, using Zygo interferometer. Edge growth on the sides and proximal end of electrodes is lower than distal corner growth. Edge growth in distal corners is the highest on the plated electrodes and represents the worst case scenario. The edge growth of pulse plated electrodes is compared with electrodes plated with constant current method used in non-pulsed plating processes (see FIG. 1). The pulsed plating techniques disclosed herein can utilize conventional methods and/or materials (see, e.g. Feltham and Spiro Chemical Reviews, 1971, Vol. 71, No. 2 pp. 177-193; Chandrasekar et al., Electrochimica Acta 53 (2008) 3313-3322; Karimi et al., Electrochemistry Communications Volume 19, June 2012, Pages 17-20; Wei et al., J. Phys. Chem. C 2007, 111, 15456-15463; and U.S. Pat. No. 4,490,219, the contents of which are incorporated by reference).

Common acronyms used in the examples include: WE Working Electrode; GOx Glucose Oxidase; HSA Human Serum Albumin; SITS Sensor In-vitro Test System; GLM Glucose Limiting Membrane (an embodiment of an analyte modulating layer); OQ Operational Qualification; SAR Surface Area Ratio; BTS Bicarbonate Test System; and EIS Electrochemical Impedance Spectroscopy. The BTS and SITS tests discussed in the example are tests used to evaluate aspects of sensor performance. SITS measures sensor signal in glucose solutions over 5-7 days, as wells as sensor oxygen response, temperature response, background current, linearity, stability, acetaminophen interference and response time. Dog tests are used to evaluate glucose sensor performance in vivo (Isig and calculated blood glucose level) in diabetic and non-diabetic dogs for up to 3 days and compares glucose level measured by continuous glucose sensors to that measured by a glucose meter.

Figure 2:
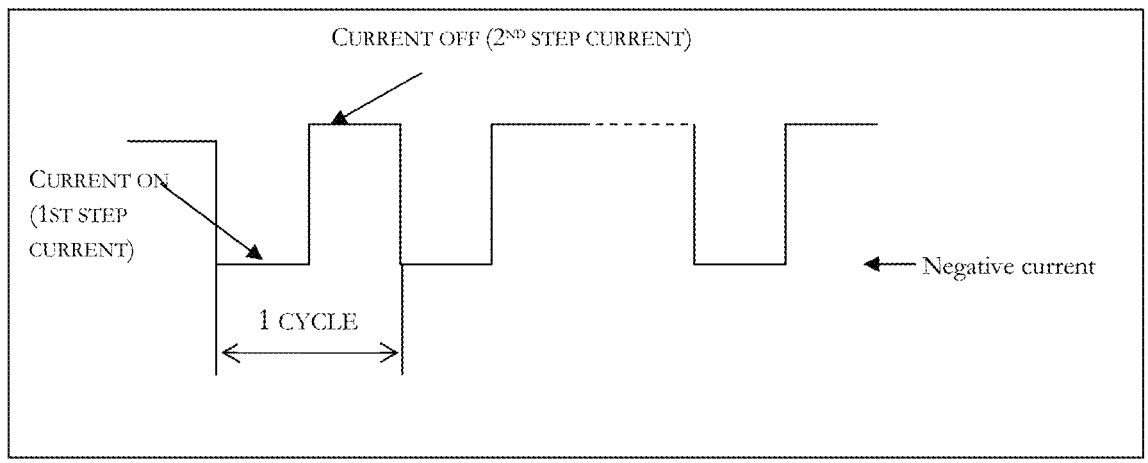
FIG. 2 provides a schematic of pulse plating variables utilized in embodiments of the invention including wave form, current, on time, off time, and number of cycles.

FIG. 2 provides a schematic of the wave form of current in pulsed current plating. Surface area and edge growth of pulse plated electrodes are affected by plating current, pulse length, duty cycle and number of cycles. Engineering plates were plated on a Gamry Potentiostat MultiEchem8 workstation ("Gamry") one WE at a time using standard platinum solutions (such as those disclosed below) and different plating parameters. For this experiment: the first step (on time) current ranged from −60 µA to −100 µA; the first step duration ranged from 1 to 5 seconds; the second step current (off time) ranged from 0 to +10 µA; the second step duration ranged from 1 to 5 seconds, and the cycle number ranged from 40 to 180. Typically, one can plate a number of electrodes (e.g. from 1 to 24) at a time using selector boards designed for use with the Gamry. One only needs to adjust the total applied current based on the number of electrodes to be plated. The current density on each electrode is the same as target current density. In illustrative embodiments using the Gamry, we used a 3-electrode setup (working electrode, counter electrode, reference electrode). Pulse plating can also be done with a two-electrode setup (working electrode, counter electrode). As noted above, in this working embodiment of the invention, a Gamry workstation was used. Those of skill in the art understand that pulse plating does not have to be done on a Gamry, and can be done on other plating modules (e.g. on a production plater), for example, those where the machine is programmed to control the applied current and time. The following text describes one manner in which it can be done on the Gamry workstation:

Submerge sensor plate in Pt plating solution. Connect Ag/AgCl electrode to Reference electrode from Gamry, Connect Pt mesh to counter electrode cable from Gamry, connect electrodes intended for Pt plating to working electrode cable from Gamry. Choose Chronopotentiometry from Gamry Instruments Framework menu. Set step 1 current to −75 uA per electrode, step 1 time to 2 seconds, step 2 current to 0, step 2 time to 2 second, and cycle number to 170.

Preparation of Illustrative Platinum Plating Solution

To make 1000 ml of solution add approximately 500 ml di water to a brown glass bottle then add 31.25 gram of $H_2PtCl_6 \cdot 1 H_2O$ and allow to dissolve in the dark. Add to this solution 109.4 mg $Pb(CH_3COO)_2 \cdot 3H_2O$. Allow added materials to totally dissolve and bring volume up to 1000 ml with di water.

Figure 3:
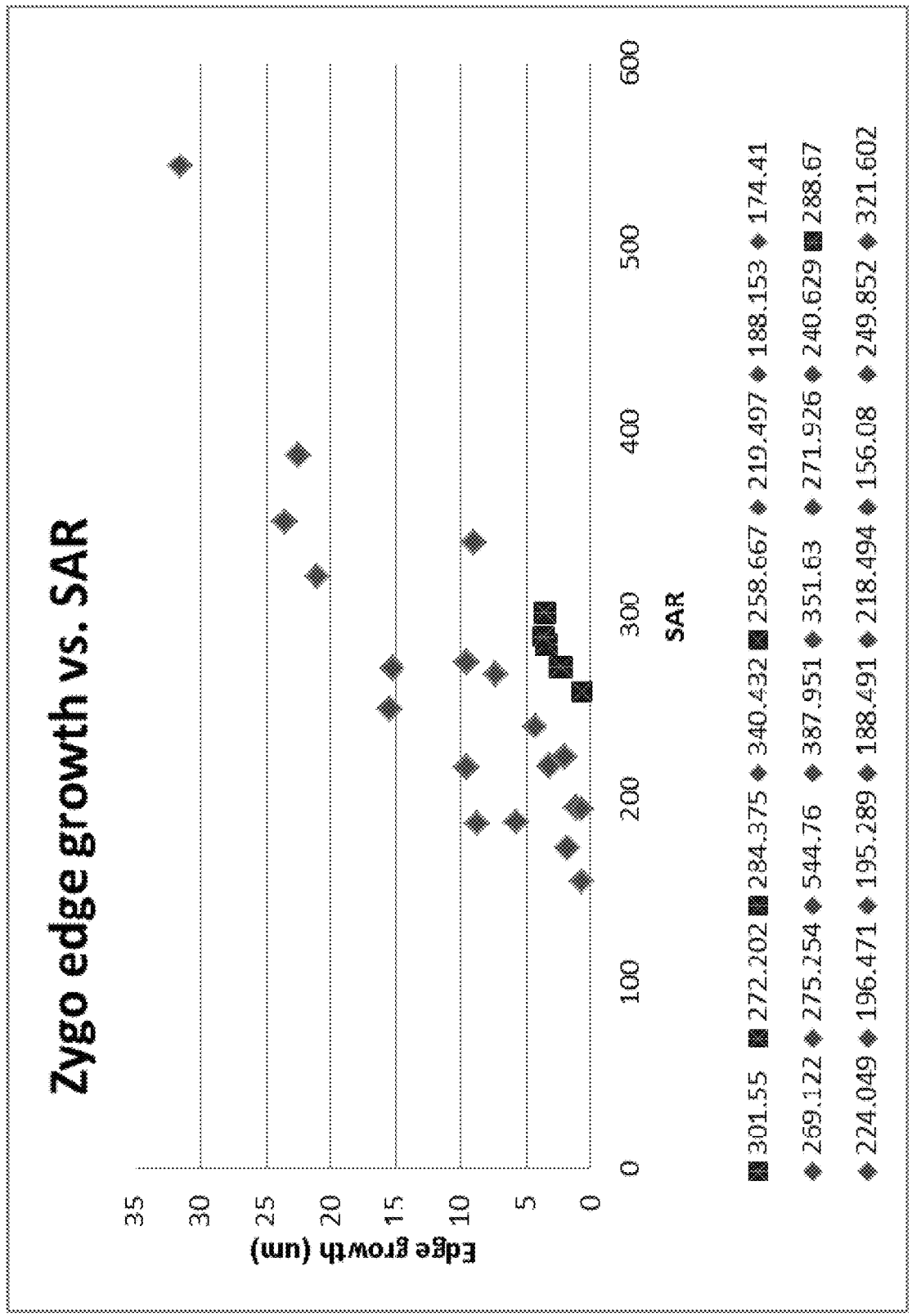
FIG. 3 provides a graph of data showing edge growth vs. surface area ratio (SAR) of electrodes plated with different process parameters. The five blue squares are electrodes that demonstrate sufficiently high SAR and significantly reduced edge growth at the same time. The conditions used on these electrodes are identified in Table 1 in the examples below. These conditions are typical for pulsed current plating of continuous glucose sensor electrodes.

FIG. 3 shows SAR and edge growth of WEs plated under various different conditions. The five squares in the center of the graph are electrodes that demonstrate sufficiently high SAR and significantly reduced edge growth at the same time. The conditions used on these electrodes are identified in Table 1 below. These conditions are useful for pulsed current plating of continuous glucose sensor electrodes.

TABLE 1

Pulsed plating conditions that produced desirable SAR and edge growth.

| Electrode ID | Current | On (s) | Off (s) | Cycles | SAR | Zygo Edge growth (uA) |
|---|---|---|---|---|---|---|
| 032112_031412_10WE | −80 | 2 | 2 | 150 | 301.55 | 3.55 |
| 032112_031412_9WE | −75 | 2 | 2 | 150 | 258.667 | 0.72 |
| 03162012_031412_16WE | −75 | 2 | 2 | 150 | 288.67 | 3.69 |
| 032112_031412_11WE | −75 | 2 | 2 | 170 | 272.202 | 2.30 |
| 032112_031412_12WE | −75 | 2 | 2 | 180 | 284.375 | 3.45 |

Figure 1B:
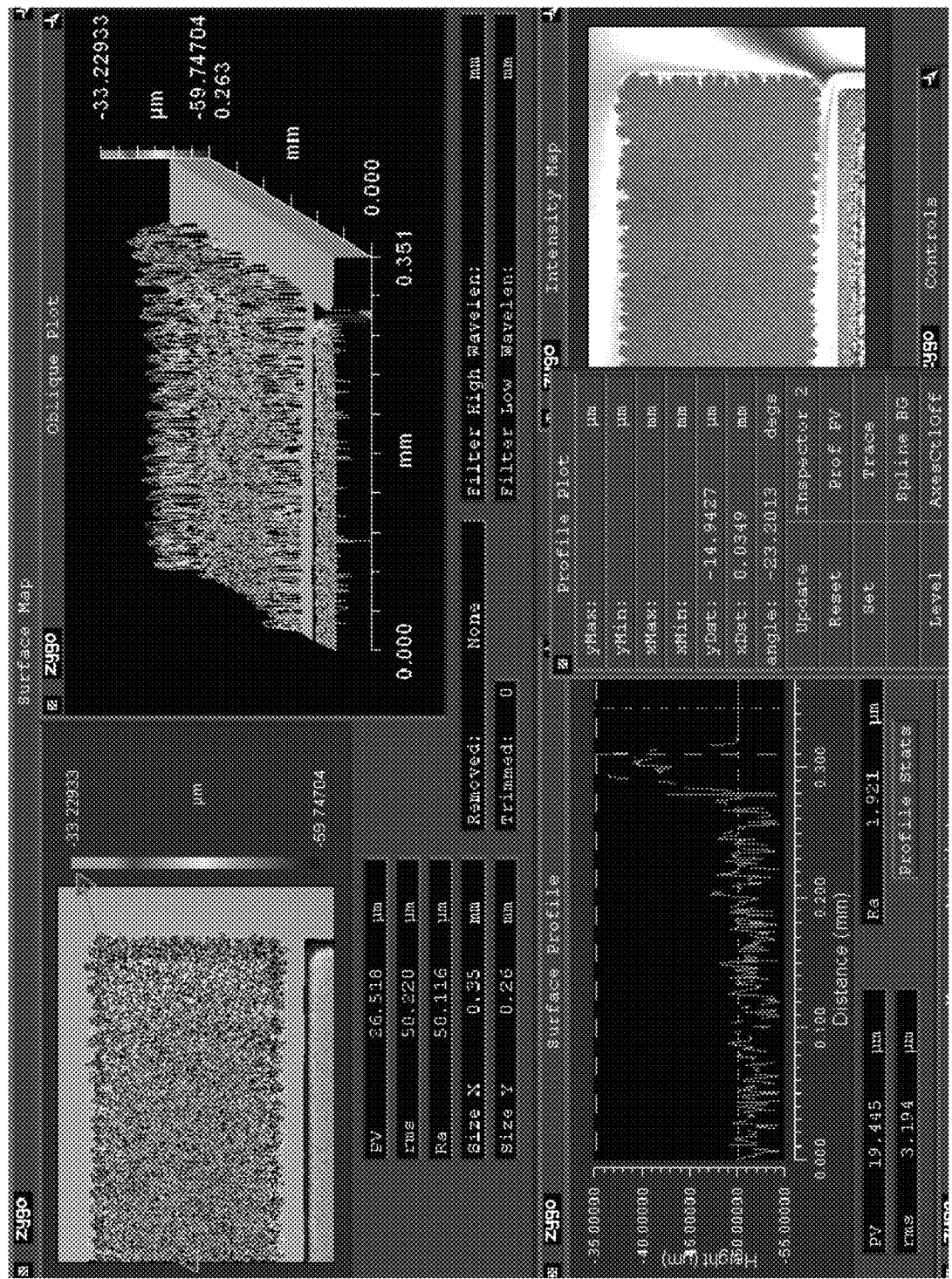
Figure 4:
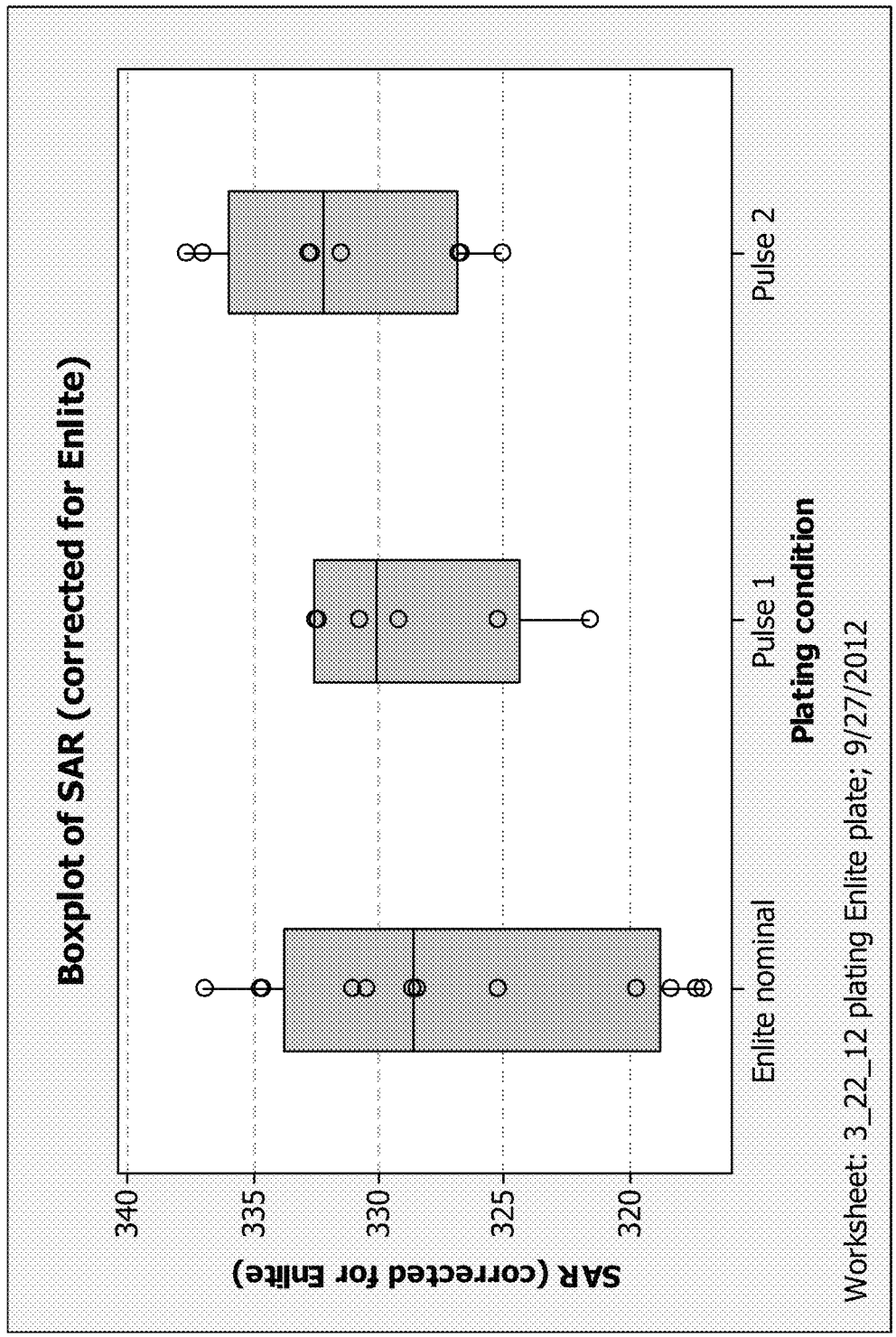
FIG. 4 provides a boxplot of WE SAR data from pulse plating methods and Enlite nominal plating methods (i.e. nonpulsed plating methods).
Figure 5:
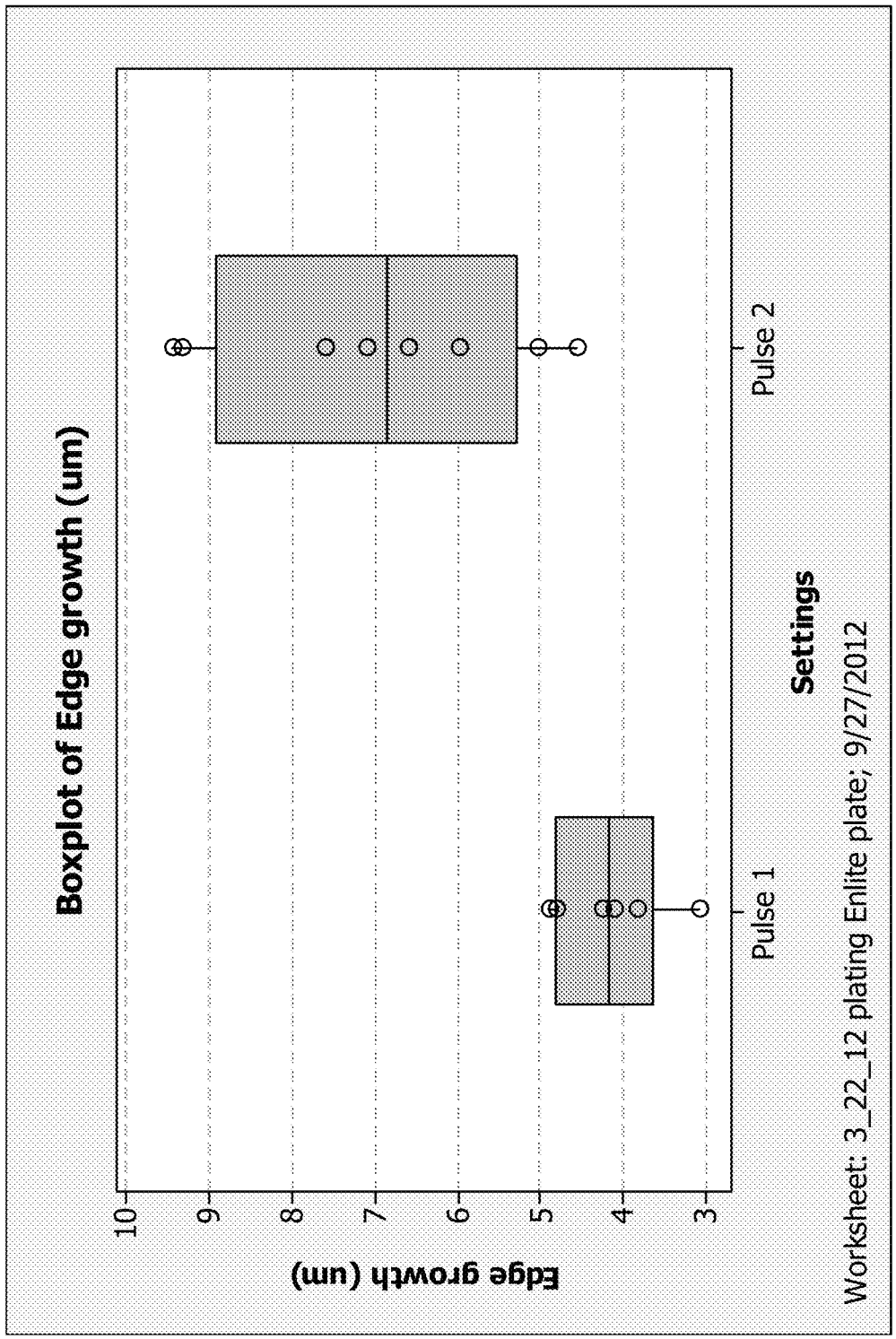
FIG. 5 provides a boxplot of data showing edge growth of pulse plated electrodes using different pulse plating parameters.

To explore and refine the conditions for pulse plating, a sensor plate comprising a base was pulsed plated on Gramry using settings shown in Table 2. In this table, the SAR of a WE made with conventional plating techniques (constant current) is included for reference. Both pulse plating conditions produced SAR matching that of conventional (constant current) plating (FIG. 4). When plating at −80 µA, it was observed that the edge growth is significantly higher, while SAR is not statistically different from plating at −75 µA (FIG. 4 and FIG. 5), therefore a current of −75 µA was chosen for all subsequent experiments when plating rectangular Enlite working electrodes (those used in Medtronic's Enlite™ Glucose Sensor). Larger electrodes and/or distributed electrodes typically require higher currents. Conventional (constant current) plating produces edge growth of about 15 to 20 µm (FIG. 1B).

TABLE 2

Settings for pulse plating

| Settings | Electrode ID | Current (µA) | On (s) | Off (s) | cycles |
|---|---|---|---|---|---|
| Pulse 1 | 2494-4 WE 14, 22, 24, 2, 3, 4 | −75 | 2 | 2 | 170 |
| Pulse 2 | 2494-4 WE 15, 16, 19, 5, 6, 7, 8, 9 | −80 | 2 | 2 | 150 |
| Enlite Nominal | 3172-12, all WE | −75 | 210 | — | — |

Figure 7:
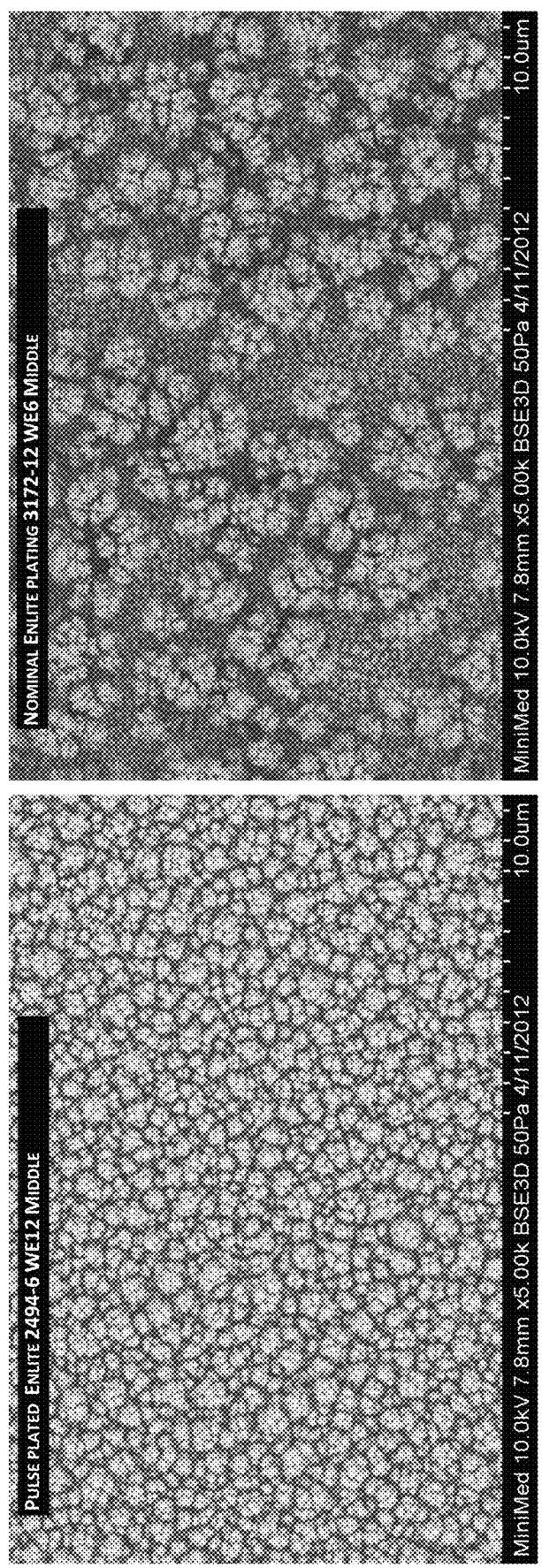
FIG. 7 provides SEM pictures showing a comparison of WEs at the same magnification: left, pulse plated Enlite electrode ($-75$ µA, 2 sec on, 2 sec off, 150 cycles), right, nominally non-pulse plated Enlite electrode.
Figure 8:
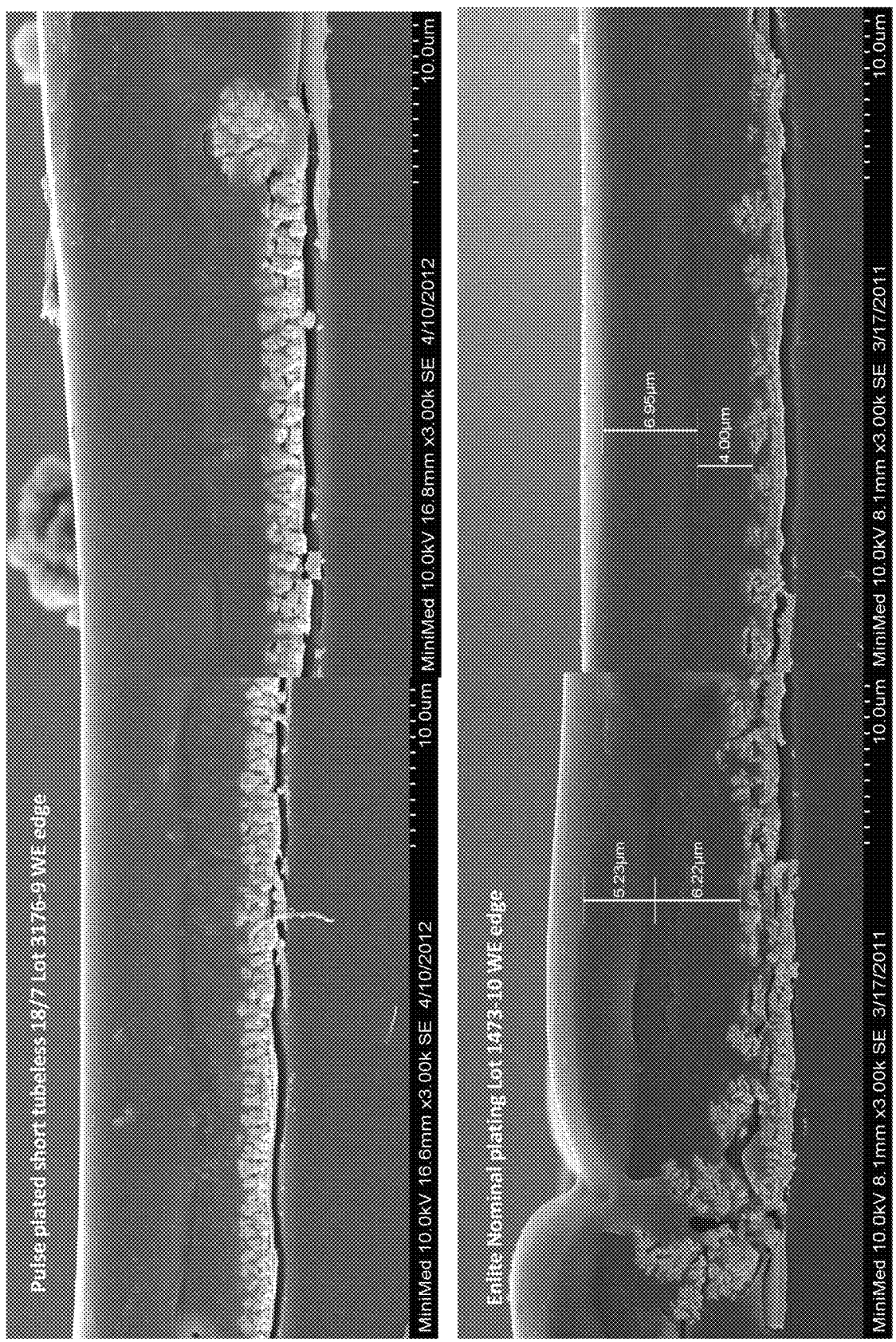
FIG. 8 provides pictures showing cross-sections of pulse plated (upper) and nominally non-pulse plated (lower) Enlite plates with chemistry layers.
Figure 9:
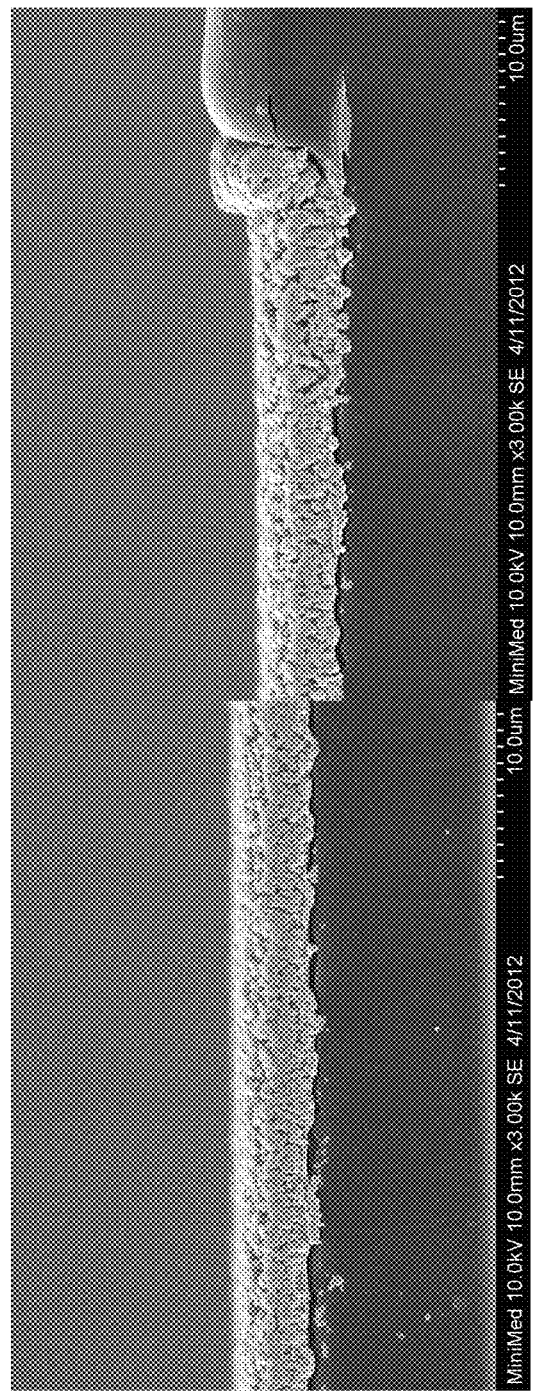
FIG. 9 provides pictures showing cross-sections of a pulse plated WEs.

FIGS. 6 and 7 are scanning electron microscope (SEM) pictures of the distal end of plated working electrodes. At the same magnification, pulse plated electrodes have drastically reduced edge growth and a more uniform appearance. FIG. 8 shows cross-sections of WE post BTS test. Pulse plated platinum has shorter dendrites but a larger number of them than conventional "Enlite nominal" plating processes that utilize constant current. This explains the sufficiently high SAR on pulse plated electrodes.

On nominally plated Enlite plate (FIG. 8), at the bottom is a thin layer of denser and smaller features, from this layer grow large dendrites. On electrode edges, dendrites grow to enormous height and width (FIG. 6, right). The pulse plated platinum (FIG. 9) shows a thicker layer of smaller features and an absence of large dendrites on either the center or edges of electrodes. On pulse plated electrodes edge growth stays below the height of polyimide insulation (5 µm for Enlite plates, 7 µm for short tubeless plates) except possibly on the two distal corners. The edge growth on distal corners of pulse plated electrodes is dramatically lower than that on Enlite nominal plated sensors.

Effect of Electrode Shape on Pulse Plating

Substrates with the same WE geometric area but different WE aspect ratio were pulse plated with the same settings: −75 µA, 2 sec on, 2 sec off, 150 cycles. These substrates are listed in Table 3. LS 02 is a special engineering substrate with 4 different aspect ratios and two electrode sizes on the same plate.

TABLE 3

Substrate plates with different WE aspect ratio

| Substrate Description | Lot Nr. | WE Aspect ratio |
|---|---|---|
| Enlite (12/5) | 2494-6 | 13.9 |
| 100% short tubeless (18/7) | 3176-8 | 7.9 |
| TLS 02 Fat WE | 3146-1, WE 1, 6, 12 | 4.5 |
| TLS 02 Narrow WE | 3146-1, WE24 | 14.0 |

The SAR is not statistically different on electrodes with the same size but different aspect ratio. Taking into account that Enlite polyimide insulation is 2 µm thinner than short tubeless or TLS 02 plates, and that edge growth is the height of platinum edge growth measured from the surface of polyimide insulation around the WE, pulse plated edge growth is not significantly different among the groups.

Illustrative Sensor Build

Sensors were built per on short tubeless plates (Table 4). Pulse plating was carried out on a Gamry Potentiostat MultiEchem8 workstation, one WE at a time. The CE and RE were then plated on a production plater using Enlite nominal settings. All electrodes for the Enlite nominal control group were plated on the production plater. The rest of sensor fabrication, assembly and sterilization followed Enlite standard fabrication and assembly procedures. "2× permeable GLM" refers to glucose limiting polymer with the twice the permeability as the GLM used in standard Enlite sensors.

TABLE 4

Sensors built at different conditions

| Plate number | WE plating | GLM dry thickness |
|---|---|---|
| 3311-10 | −75 uA, 2 s on, 2 s off, 170 cycles | 7 µm 2x permeable |
| 3311-11 | Enlite nominal control, −75 uA, 210 s | 7 µm 2x permeable |
| 3313-1, 2 | −75 uA, 2 s on, 2 s off, 170 cycles | 8 µm 2x permeable |
| 3313-3, 4 | −75 uA, 2 s on, 2 s off, 170 cycles | 10 µm 2x permeable |

SITS Test

Figure 15:
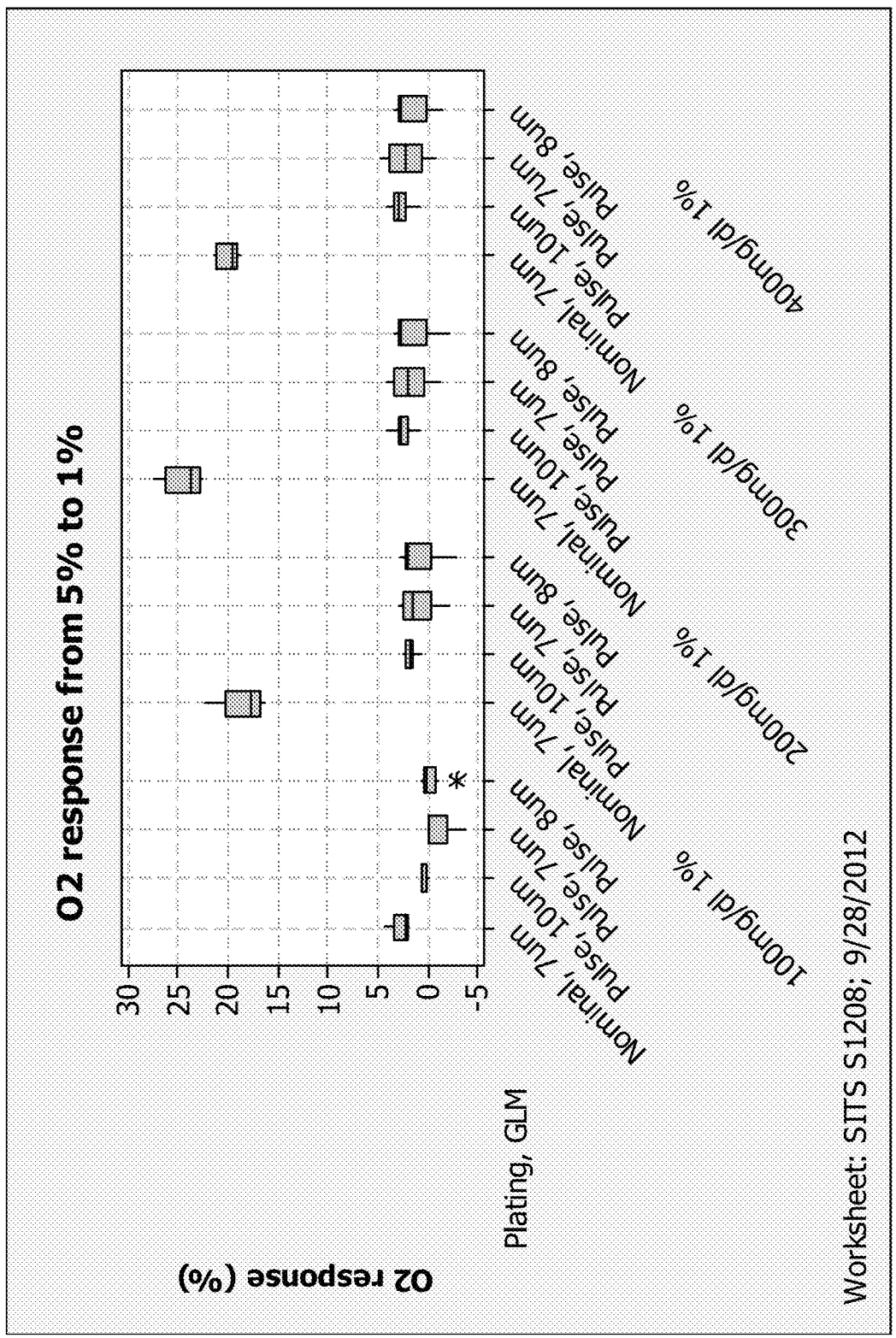
FIG. 15 provides a boxplot of data of $O_2$ responses from 5% to 1% and a differing glucose concentration in electrodes made from various pulse plating methods and nonpulsed (nominal) plating methods.
Figure 16:
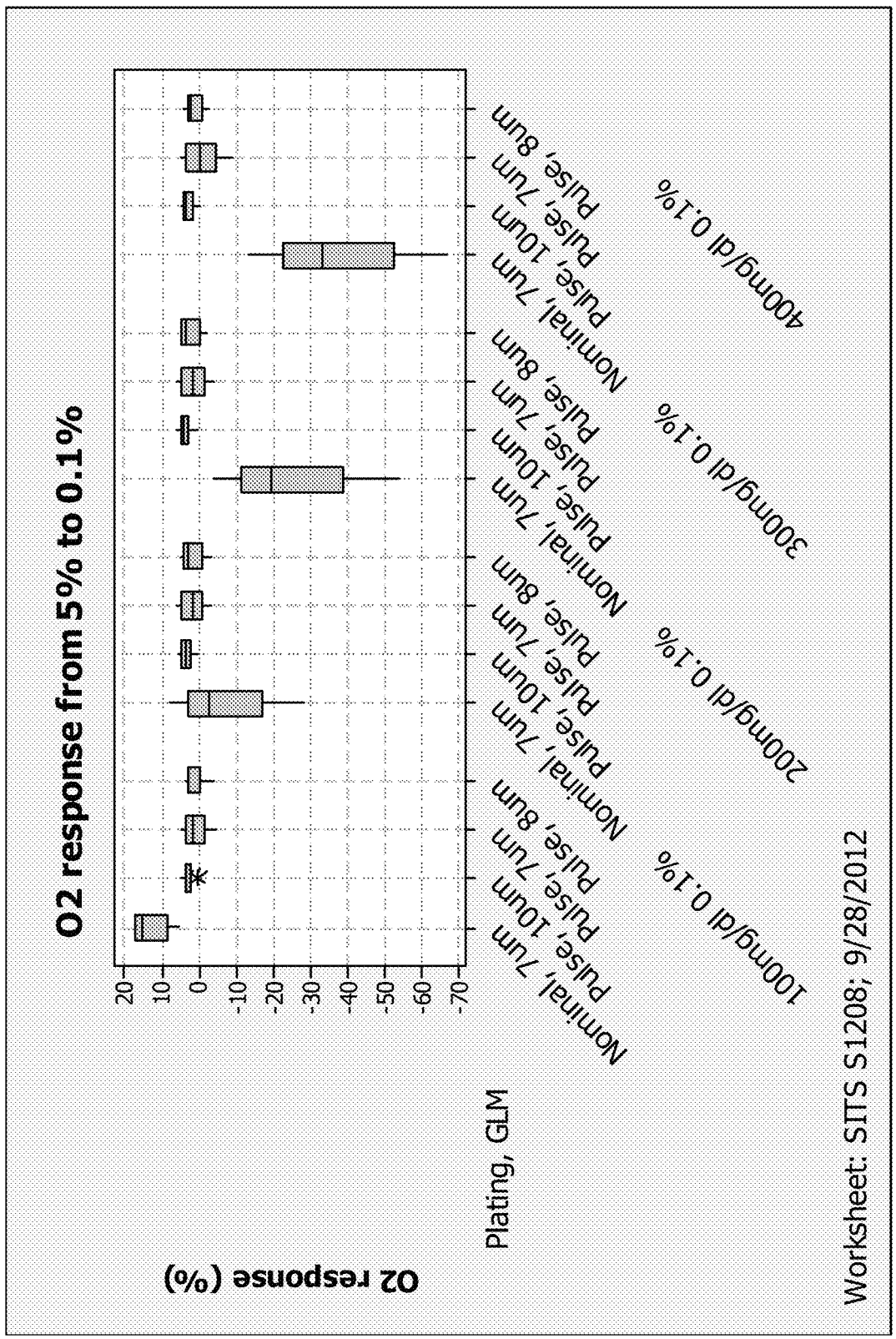
FIG. 16 provides a boxplot of data of $O_2$ responses from 5% to 0.1% and a differing glucose concentration in electrodes made from various pulse plating methods and nonpulsed (nominal) plating methods.
Figure 17:
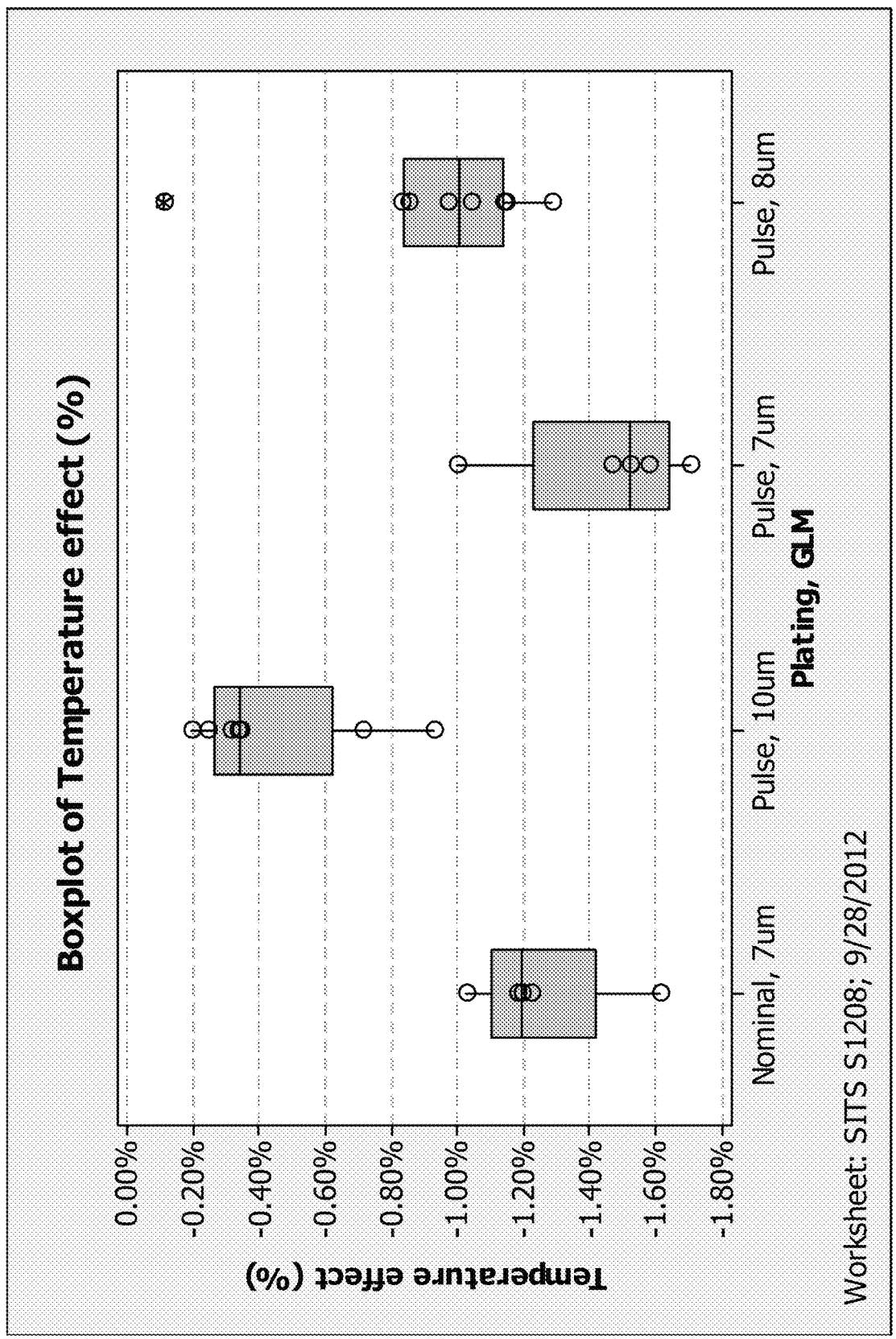
FIG. 17 provides a boxplot of the effect of temperature (signal change per degree F.) on electrodes made from various pulse plating methods and nonpulsed (nominal) plating methods.

Five sensors per group from Table 4 were tested via SITS. Key performance parameters are calculated and shown in FIG. 13 to FIG. 18. Pulse plated sensors show higher signal and higher day-1 background current than comparative control electrodes. Pulse plated sensor also have lower or similar acetaminophen interference to comparative control electrodes. The most distinguishing characteristic of pulse plated WE is the $O_2$ response. All pulse plated sensors have more muted oxygen response than comparative controls (FIGS. 15 and 16). When oxygen level is changed from 5% to an extremely low 0.1%, the oxygen response of comparative controls is no longer "inversed" and sensor signal becomes very low. At this $O_2$ level, the pulse plated sensors have on average less than 5% change in signal compared to the signal at 5% oxygen. This is a great advantage because oxygen level in the human body is susceptible to changes, and signal from the continuous glucose sensors should accurately reflect glucose level in the body, not oxygen level.

It is not well understood why pulse plating suppresses oxygen response. Without being bound by a specific theory or mechanism of action, one possible reason is that because the edge growth is almost eliminated on pulse plated WE, the chemistry layer thickness is more uniform. Working embodiments of the glucose sensors disclosed herein include a GLM layer designed to limit the diffusion of glucose without limiting the diffusion of oxygen to the electrode surface (in order for the reactions between glucose and glucose oxidase coated on the WE to be glucose limited). On WE plated with constant current (nominal Enlite GLOBAL plating), there are areas of very thin GLM at the sites of edge growth, allowing the local glucose concentration on the electrode side to become much higher than what the sensors are designed to handle. The high local glucose concentration could have depleted the available oxygen, making the reaction rate on WE surface oxygen limited rather than glucose limited. Pulse plating of WE eliminated the thin areas of GLM, this may be the reason the sensor signal have a muted response to oxygen level change. Moreover, when using non-pulse plating methods to form multiple electrodes (e.g. a WE and a RE) in proximity, if the edge growth is too high, there is risk shorting these electrodes, because edge growth can also grow laterally.

It is to be understood that this invention is not limited to the particular embodiments described, as such may, of course, vary. It is also to be understood that the terminology used herein is for the purpose of describing particular embodiments only, and is not intended to be limiting, since the scope of the present invention will be limited only by the appended claims. In the description of the preferred embodiment, reference is made to the accompanying drawings which form a part hereof, and in which is shown by way of illustration a specific embodiment in which the invention may be practiced. It is to be understood that other embodiments may be utilized and structural changes may be made without departing from the scope of the present invention.

The descriptions and specific examples, while indicating some embodiments of the present invention are given by way of illustration and not limitation. Many changes and modifications within the scope of the present invention may be made without departing from the spirit thereof, and the invention includes all such modifications.

The invention claimed is:

1. A method of making an analyte sensor apparatus, the method comprising the steps of:
   providing a base substrate formed from a planar sheet of a dielectric material and having a well disposed therein;
   forming a working electrode in the well of the base substrate, wherein the working electrode comprises a platinum composition formed from an electrodeposition process comprising depositing platinum black in the well using a plurality of electric current pulses selected so that:
      the platinum composition comprises a central planar region having a first thickness and an edge region having a second thickness that surrounds the central planar region; and
      the average thickness of the platinum black layer in the edge region is less than 2× the average thickness of the platinum black layer in the central planar region, so that the working electrode mutes oxygen response and reduces edge growth while operating the analyte sensor;
   forming an analyte sensing layer on the working electrode, wherein the analyte sensing layer detectably alters the electrical current at the working electrode in the presence of an analyte; and
   forming an analyte modulating layer on the analyte sensing layer, wherein the analyte modulating layer modulates the diffusion of analyte therethrough;
   so that the analyte sensor apparatus is formed.

2. The method of claim 1, wherein:
   the platinum composition is formed from a process comprising depositing platinum black in the well using a plurality of at least 50, 100 or 150 electric current pulses;
   the current is applied in a wave form;
   the duration of the pulses is from 1 to 5 seconds; and/or
   the electrical current of the pulses is from −60 μA to −100 μA or from 0 μA to 10 μA.

3. The method of claim 1, wherein:
   the analyte sensor apparatus is an amperometric glucose sensor;
   the amperometric glucose sensor generates a first signal in a solution comprising 100 mg/dL glucose and 5% oxygen;
   the amperometric glucose sensor generates a second signal in a solution comprising 100 mg/dL glucose and 0.1% oxygen; and
   the first signal and the second signal differ by less than 10%.

4. The method of claim 1, wherein:
   the base substrate is formed so that the well comprises a lip surrounding the well; and
   the edge region of the platinum black composition is below the lip of the well.

5. The method of claim 1, further comprising:
   forming a working electrode, a counter electrode and a reference electrode on the base substrate;
   forming a plurality of contact pads on the base substrate; and
   forming a plurality of electrical conduits on the base substrate.

6. The method of claim 1, wherein:
   the working electrode is formed as an array of electrically conductive members disposed on the base substrate;
   the electrically conductive members are circular and have a diameter between 10 μm and 400 μm; and
   the array comprises at least 10 electrically conductive members.

7. The method of claim 1, wherein the method comprises forming a plurality of working electrodes, counter electrodes and reference electrodes clustered together in units consisting essentially of one working electrode, one counter electrode and one reference electrode are formed on the base substrate; and
   the clustered units are longitudinally distributed on at least one longitudinal arm of the base substrate in a repeating pattern of units.

8. The method of claim 7, wherein the wherein the electrodeposition process is selected to produce a platinum black layer having an average thickness between 1 μm and 10 μm in the central planar region.

9. The method of claim 1, wherein:
   the analyte sensing layer comprises glucose oxidase;
   the apparatus comprises an adhesion promoting layer disposed between the analyte sensing layer and the analyte modulating layer; or
   the analyte modulating layer comprises a hydrophilic comb-copolymer having a central chain and a plurality of side chains coupled to the central chain, wherein at least one side chain comprises a silicone moiety.

10. A method of making an analyte sensor apparatus, the method comprising the steps of:
    providing a base substrate formed from a planar sheet of a dielectric material and having a well disposed therein;
    forming a working electrode in the well of the base substrate, wherein the working electrode comprises a platinum composition formed from an electrodeposition process comprising depositing platinum black in the well using a plurality of electric current pulses selected so that:
       the platinum composition comprises a central planar region having a first thickness and an edge region having a second thickness that surrounds the central planar region;
       the central planar region and the edge region comprise platinum dendrites;
       the first thickness is different from the second thickness; and
       the average thickness of the platinum black layer in the edge region is less than 2× the average thickness of the platinum black layer in the central planar region so that the working electrode mutes oxygen response and reduces edge growth while operating the analyte sensor;
    forming an analyte sensing layer on the working electrode, wherein the analyte sensing layer detectably alters the electrical current at the working electrode in the presence of an analyte; and
    forming an analyte modulating layer on the analyte sensing layer, wherein the analyte modulating layer modulates the diffusion of analyte therethrough;
    so that the analyte sensor apparatus is formed.

11. The method of claim 10, wherein:
    the well comprises a lip surrounding the well; and
    the edge region of the platinum black composition is below the lip of the well.

12. The method of claim 10, wherein the average thickness of the platinum black layer in the central planar region is formed to be between 1 μm and 10 μm.

13. The method of claim 10, wherein the well is rectangular or circular.

14. The method of claim 10, wherein:
the working electrode is formed from a plurality of electrically conductive members disposed in the base layer in an array;
the electrically conductive members comprise circular discs having a diameter from 1 μm to 400 μm; and and
the array of electrically conductive members is coupled to an electrical conduit.

15. The method of claim 10, wherein:
the base substrate comprises a plurality of reference electrodes, a plurality of working electrodes and a plurality of counter electrodes clustered together in units consisting essentially of one working electrode, one counter electrode and one reference electrode; and
the clustered units are longitudinally distributed on the base substrate in a repeating pattern of units.

16. The method of claim 10, further comprising coupling the analyte sensor apparatus to a biocompatible material adapted to contact a tissue interface when implanted in vivo.

17. The method of claim 10, further comprising coupling the analyte sensor apparatus to a system comprising:
a processor;
a computer-readable program code having instructions, which when executed cause the processor to:
assess electrochemical signal data obtained from the working electrode; and
compute analyte concentrations based upon the electrochemical signal data obtained from the working electrode.

18. The method of claim 10, wherein:
the platinum composition is formed from a process comprising depositing platinum black in the well using a plurality of at least 50, 100 or 150 electric current pulses;
the current is applied in a wave form;
the duration of the pulses is from 1 to 5 seconds; and/or
the electrical current of the pulses is from −60 μA to −100 μA or from 0 μA to 10 μA.

19. The method of claim 18, wherein the wherein the electrodeposition process is selected to produce a platinum black layer having an average thickness between 1 μm and 10 μm in the central planar region.

20. The method of claim 10, wherein:
the analyte sensor apparatus is an amperometric glucose sensor;
the amperometric glucose sensor generates a first signal in a solution comprising 100 mg/dL glucose and 5% oxygen;
the amperometric glucose sensor generates a second signal in a solution comprising 100 mg/dL glucose and 0.1% oxygen; and
the first signal and the second signal differ by less than 10%.

* * * * *